United States Patent
Andersen et al.

(10) Patent No.: US 6,582,462 B1
(45) Date of Patent: *Jun. 24, 2003

(54) VALVE PROSTHESIS FOR IMPLANTATION IN THE BODY AND A CATHETER FOR IMPLANTING SUCH VALVE PROSTHESIS

(75) Inventors: Henning Rud Andersen, Hoejbjerg (DK); John Michael Hasenkam, Aarhus V (DK); Lars Lyhne Knudsen, Aarhus C (DK)

(73) Assignee: Heartport, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/514,426

(22) Filed: Feb. 28, 2000

Related U.S. Application Data

(63) Continuation of application No. 09/026,574, filed on Feb. 20, 1998, now Pat. No. 6,168,614, which is a continuation of application No. 08/955,228, filed on Oct. 21, 1997, now abandoned, which is a division of application No. 08/801,036, filed on Feb. 19, 1997, now Pat. No. 5,840,081, which is a continuation of application No. 08/569,314, filed on Dec. 8, 1995, now abandoned, which is a continuation of application No. 08/352,127, filed on Dec. 1, 1994, now abandoned, which is a division of application No. 08/261,235, filed on Jun. 14, 1994, now Pat. No. 5,411,552, which is a continuation of application No. 07/961,891, filed as application No. PCT/DK91/00134 on Mar. 16, 1991, now abandoned.

(30) Foreign Application Priority Data

May 18, 1990 (DK) .............................. 1246/90

(51) Int. Cl.⁷ .................................................. A61F 2/24
(52) U.S. Cl. ...................................... 623/1.26; 623/2.14
(58) Field of Search ................................. 623/FOR 101, 623/2.1–2.19, 2.38–2.41, 900, 904, 1.24–1.26

(56) References Cited

U.S. PATENT DOCUMENTS

| | | |
|---|---|---|
| 2,055,188 A | 4/1934 | Wapler et al. |
| 3,409,013 A | 11/1968 | Berry |
| 3,587,115 A | 6/1971 | Shiley |

(List continued on next page.)

FOREIGN PATENT DOCUMENTS

| | | | |
|---|---|---|---|
| DE | 2246526 | 3/1973 | |
| EP | 0103546 A1 | 3/1984 | |
| EP | 0350302 | 1/1990 | |
| EP | 0357003 | 3/1990 | |
| EP | 0592410 B1 | 10/1995 | |
| GB | 2056023 | 3/1981 | |
| RU | 1258406 | 9/1986 | |
| RU | 1271508 | 11/1986 | |
| RU | 1371701 | 2/1988 | |
| SU | 1271508 A | * 11/1986 | ........ 623/FOR 101 |
| WO | WO9117720 | 11/1991 | |
| WO | WO9217118 | 10/1992 | |

OTHER PUBLICATIONS

Fishman et al., "Prevention of Prothetic Cardiac Valve Detachment", Surgery, vol. 67, No. 5, pp. 867–873, May 1970.*

16th Ediiton of The Merck Manual of Diagnosis and Therapy (1992) "Valvular Heart Disease," pp. 546–553.

Yamaguchi, Case Description "A Case of a Reoperation Using a Balloon Catheter with Blocked Pars Ascendes Aortae" Kyobu Geka, Oct. 1989, 42:11, pp. 961–964.

World Medical Manufacturing Corp., Talent Endovascular Bifurcated Spring Graft System Composite Design brochure, no date.

Derwent Abstract No. 87–1980867/27 (1987), SU 1271508 (Gorkii Kirov Medical Ins.).

*Primary Examiner*—David H. Willse

(57) ABSTRACT

A valve prosthesis for implantation in the body by use of a catheter includes a stent made from an expandable cylinder-shaped thread structure having several spaced apices. The elastically collapsible valve is mounted on the stent as the commissural points of the valve are secured to the projecting apices.

8 Claims, 4 Drawing Sheets

U.S. PATENT DOCUMENTS

| | | | |
|---|---|---|---|
| 3,657,744 A | * | 4/1972 | Ersek .................... 623/902 X |
| 3,671,979 A | | 6/1972 | Moulopoulos |
| 3,714,671 A | | 2/1973 | Edwards et al. |
| 3,755,823 A | | 9/1973 | Handcodk |
| 3,799,150 A | | 3/1974 | Bonnet |
| 4,035,849 A | | 7/1977 | Angell et al. |
| 4,038,703 A | | 8/1977 | Bokros |
| 4,056,854 A | * | 11/1977 | Boretos et al. ............ 623/2.18 |
| 4,106,129 A | | 8/1978 | Carpentier et al. |
| 4,222,126 A | | 9/1980 | Boretos et al. |
| 4,297,749 A | | 11/1981 | Davis et al. |
| 4,339,831 A | | 7/1982 | Johnson |
| 4,343,048 A | | 8/1982 | Ross |
| 4,391,282 A | | 7/1983 | Ando et al. |
| 4,470,157 A | | 9/1984 | Love |
| 4,574,803 A | | 3/1986 | Storz |
| 4,580,568 A | | 4/1986 | Gianturco |
| 4,592,340 A | | 6/1986 | Boyles |
| 4,612,011 A | | 9/1986 | Kautzky |
| 4,655,771 A | | 4/1987 | Wallsten |
| 4,692,164 A | | 9/1987 | Dzemeshkevich et al. |
| 4,725,274 A | | 2/1988 | Lane et al. |
| 4,731,074 A | | 3/1988 | Rousseau et al. |
| 4,733,665 A | | 3/1988 | Palmaz |
| 4,777,951 A | | 10/1988 | Cribier et al. |
| 4,778,461 A | | 10/1988 | Pietsch et al. |
| 4,787,899 A | | 11/1988 | Lazarus |
| 4,787,901 A | | 11/1988 | Baykut |
| 4,790,843 A | | 12/1988 | Carpentier et al. |
| 4,796,629 A | | 1/1989 | Grayzel |
| 4,830,003 A | | 5/1989 | Wolff et al. |
| 4,851,000 A | | 7/1989 | Gupta |
| 4,856,516 A | | 8/1989 | Hillstead |
| 4,878,495 A | | 11/1989 | Grayzel |
| 4,878,906 A | | 11/1989 | Lindemann et al. |
| 4,883,458 A | | 11/1989 | Shiber |
| 4,892,541 A | | 1/1990 | Alonso |
| 4,917,698 A | | 4/1990 | Carpentier et al. |
| 4,932,965 A | | 6/1990 | Phillips |
| RE33,258 E | | 7/1990 | Onik |
| 4,966,604 A | | 10/1990 | Reiss |
| 4,979,939 A | | 12/1990 | Shiber |
| 4,986,830 A | | 1/1991 | Owens et al. |
| 4,994,077 A | * | 2/1991 | Dobben ...................... 623/2.2 |
| 5,007,896 A | | 4/1991 | Shiber |
| 5,019,102 A | | 5/1991 | Hoene |
| 5,026,366 A | | 6/1991 | Leckrone |
| 5,032,128 A | | 7/1991 | Alonso |
| 5,037,434 A | | 8/1991 | Lane |
| 5,041,130 A | | 8/1991 | Cosgrove et al. |
| 5,047,041 A | | 9/1991 | Samuels |
| 5,059,177 A | | 10/1991 | Towne et al. |
| 5,061,277 A | | 10/1991 | Carpentier et al. |
| 5,085,635 A | | 2/1992 | Cragg |
| 5,089,015 A | | 2/1992 | Ross |
| 5,104,407 A | | 4/1992 | Lam et al. |
| 5,123,919 A | | 6/1992 | Sauter et al. |
| 5,147,391 A | | 9/1992 | Lane |
| 5,152,771 A | | 10/1992 | Sabbaghian et al. |
| 5,163,953 A | | 11/1992 | Vince |
| 5,163,955 A | | 11/1992 | Love et al. |
| 5,167,628 A | | 12/1992 | Boyles |
| 5,201,880 A | | 4/1993 | Wright et al. |
| 5,258,021 A | | 11/1993 | Duran |
| 5,258,023 A | | 11/1993 | Reger |
| 5,295,958 A | | 3/1994 | Shturman |
| 5,306,296 A | | 4/1994 | Wright et al. |
| 5,332,402 A | | 7/1994 | Teitelbaum |
| 5,332,403 A | | 7/1994 | Kolff |
| 5,344,442 A | | 9/1994 | Deac |
| 5,350,420 A | | 9/1994 | Cosgrove et al. |
| 5,376,112 A | | 12/1994 | Duran |
| 5,376,113 A | | 12/1994 | Jansen et al. |
| 5,397,351 A | | 3/1995 | Pavcnik et al. |
| 5,411,552 A | | 5/1995 | Andersen et al. |
| 5,443,446 A | | 8/1995 | Shturman |
| 5,449,384 A | | 9/1995 | Johnson |
| 5,469,868 A | | 11/1995 | Reger |
| 5,480,424 A | | 1/1996 | Cox |
| 5,489,298 A | | 2/1996 | Love et al. |
| 5,545,209 A | | 8/1996 | Roberts et al. |
| 5,609,626 A | | 3/1997 | Quijano et al. |
| 5,755,782 A | | 5/1998 | Love et al. |
| 5,824,061 A | | 10/1998 | Quijano et al. |
| 5,840,081 A | | 11/1998 | Andersen et al. |
| 6,283,993 B1 | | 9/2001 | Cosgrove et al. |

* cited by examiner

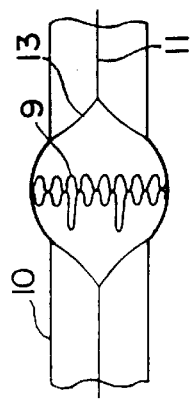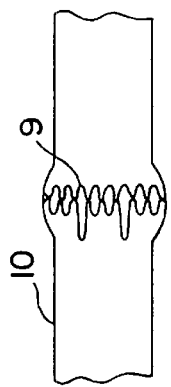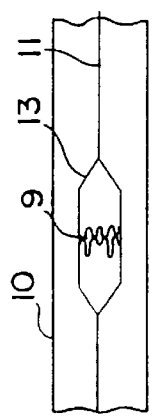
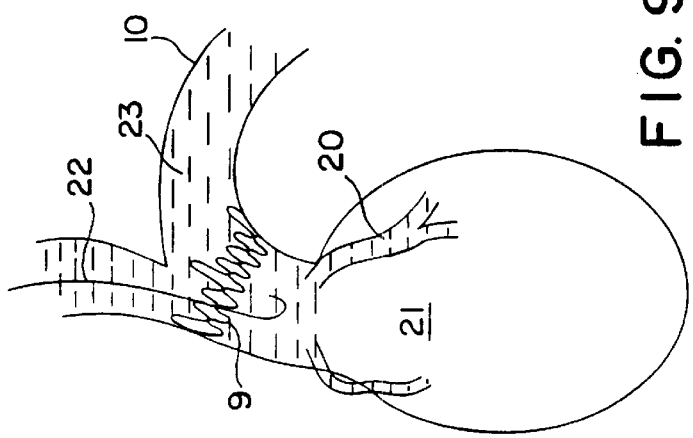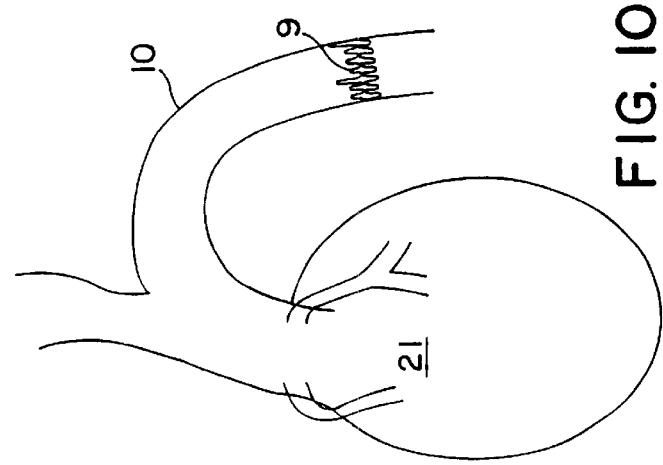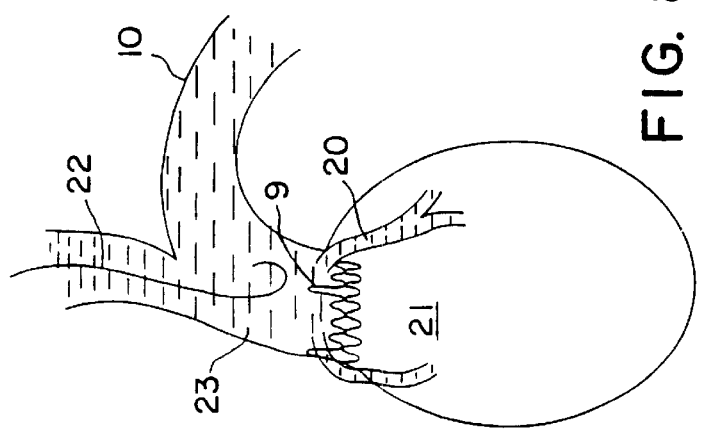

VALVE PROSTHESIS FOR IMPLANTATION IN THE BODY AND A CATHETER FOR IMPLANTING SUCH VALVE PROSTHESIS

CROSS REFERENCE TO RELATED APPLICATION

This application is a continuation of application Ser. No. 09/026,574, filed Feb. 20, 1998, now U.S. Pat. No. 6,168,614, which is a continuation of application Ser. No. 08/955,228, filed Oct. 21, 1997, now abandoned, which is a division of application Ser. No. 08/801,036, filed Feb. 19, 1997, now U.S. Pat. No. 5,840,081, which is a continuation of application Ser. No. 08/569,314, filed Dec. 8, 1995, now abandoned, which is a continuation of application Ser. No. 08/352,127, filed Dec. 1, 1994, now abandoned, which is a division of application Ser. No. 08/261,235, filed Jun. 14, 1994, now U.S. Pat. No. 5,411,552, which is a continuation of application Ser. No. 07/961,891, filed Jan. 11, 1993, now abandoned which is based on PCT/DK91/00134, filed Mar. 16, 1991.

BACKGROUND OF THE INVENTION

The present invention relates to a valve prosthesis, preferably a cardiac valve prosthesis, for implantation in the body and comprising a collapsible elastic valve which is mounted on an elastic stent wherein the commissural points of the elastic collapsible valve are mounted on the cylinder surface of the elastic stent.

Valve prostheses of this type are usually implanted in one of the channels of the body to replace a natural valve. In the present description the invention will be explained in connection with a cardiac valve prosthesis for implantation in aorta. However, it will be possible to use a valve prosthesis according to the invention in connection with implantation in other channels in the body by using the same technique as the one used for implantation of cardiac valve prosthesis. Such an implantation may, e.g., comprise the implantation of:

1. a valve (for instance a cardiac valve) in the veins,
2. a valve in the esophagus and at the stomach,
3. a valve in the ureter and/or the vesica,
4. a valve in the biliary passages,
5. a valve in the lymphatic system, and
6. a valve in the intestines.

An existing natural valve in the body is traditionally replaced with a valve prosthesis by a surgical implantation. However, a surgical implantation is often an exacting operation. Thus, today the implantation of cardiac valves are solely made by surgical technique where the thoracic cavity is opened. The operation calls for the use of a heart and lung machine for external circulation of the blood as the heart is stopped and opened during the surgical intervention and the artificial cardiac valves are subsequently sewed in.

Due to its exacting character, it is impossible to offer such operation to certain people. For instance, this is due to the fact that the person is physically weak because of age or illness. Moreover, the number of heart and lung machines available at a hospital will be a substantially limiting factor.

Cardiac valve prostheses that need no surgical intervention are known as there are used for implantation by means of a technique of catheterization. Examples of such valve prostheses are described in U.S. Pat. Nos. 3,671,979 and 4,056,854. However, both of these valve prostheses are connected to means which lead to the surface of the patient either for a subsequent activation of the valve or for a subsequent reposition or removal of the valve prosthesis. With these valve prostheses it is impossible to make an implantation which makes it possible for the patient to resume a substantially normal life in the same way as it is possible in connection with a surgical implantation of a cardiac valve.

From U.S. Pat. No. 3,755,823 an elastic stent for a cardiac valve prosthesis is known. However, this valve prostheses is not designed for implantation in the body by catheterization. Even though this patent contains no detailed explanation, the description indicates that this valve prosthesis is designed for implantation and sewing on by a surgical intervention.

Moreover, from U.S. Pat. Nos. 4,856,516 and 4,733,665 different shapes of expandable stents are known. These stents are made to be expanded by impression of a radially outward force coming from a balloon catheter or the like. These stents are made to reinforce the wall when there is a risk that the channel is closed and/or compressed.

The nearest prior art may be that the described in GB-A-2.056,023. This document discloses an elastic stent as described by way of introduction. Thus, the stent described comprises an elastic collapsible valve mounted on the cylinder surface of a cylindrical stent. However, the valve prosthesis including the stent is designated for mounting through a surgical intervention. Even though the stent is slightly collapsible, it will not be suited for implantation by a catheterization procedure.

SUMMARY OF THE INVENTION

It is the object of the present invention to provide a valve prosthesis of the type mentioned in the introductory part, which permits implantation without surgical intervention in the body and by using a catheter technique known per se and which makes it possible for the patient to resume a substantially normal life.

This is achieved according to the invention with a valve prosthesis of the type mentioned in the introductory part, which is characterized in that the stent is made from a radially collapsible and re-expandable cylindrical support means for folding and expanding together with the collapsible valve for implantation in the body by means of a technique of catheterization.

The collapsible elastic valve is mounted on the stent for instance by gluing, welding or by means of a number of suitable sutures.

If the support means are made from a thread structure, this can for instance be grate shaped, loop shaped or helical. This makes it possible to compress the stent and the collapsible valve mounted thereon for placing on the insertion catheter. The use of a non-self-expandable stent may, e.g., be effected by a compression of the stent around the expansion arrangement of the catheter which preferably consists of a balloon. When using a self-expandable stent, a catheter with an expansion arrangement is not used. In this case the stent is compressed and is inserted into an insertion or protection cap from which the stent is eliminated after implantation in order to obtain an expansion due to the stresses in the compressed support means, which for instance may be made from plastics or metal. After the compression the entire outer dimension is relatively small, which makes it possible to introduce the valve prostheses through a channel in the body.

When the valve prosthesis is introduced and placed correctly, the stent is expanded by self-expansion or by means of the expansion arrangement until the stent is given an outer dimension which is slightly larger than the channel in which it is placed. As the stent is elastic, a contraction of the stent is prevented once it is expanded. The stiffness in the material of the support means contributes to maintain the expanded shape of the stent. After the expansion is made, the expansion arrangement of the catheter is contracted and the catheter can be removed from the channel. The inlet opening can subsequently be closed and the patient will then be able to resume a normal life.

The valve prosthesis according to the invention does not require an actual operation but merely a small intervention to optionally expose the body channel, e.g., a vein, through which the insertion takes place. Thus, patients for whom an operation would be associated with high risk can be offered implantation of, for instance, cardiac valves. After the implantation has taken place, the after-treatment will advantageously be shorter than normal, which means fewer hospital days for the patient. Moreover, it is assumed that it will be possible to implant the valve prosthesis under local anaesthetic.

The valve prosthesis can be used to replace a natural valve or to establish a new valve function in one of the channels in the body which do not naturally contain a valve. For instance this goes for veins (arteries and veins) on a place without natural valves. The function of the valve prosthesis is then to ensure that the blood flows in one direction only. The valve is meant to be used in veins in the legs of persons suffering from varicose veins (varices).

In persons having varicose veins the blood flows in a wrong direction, viz. from the central veins in the center of the leg towards the superficial veins. Among other things, this is due to the changed pressure in the legs, upright working position and other conditions. A valve prosthesis according to the invention may easily be placed in the veins and prevent the flow of the blood in a wrong direction.

Also, the valve prosthesis can be used in connection with diseases, for instance cancerous tumors, where too much humour is produced. If the humour is able to flow from the cancerous tumor through several channels, it is possible to drain the humour in one desired direction through the channels of the body by an appropriate placing of the valve prosthesis.

When the valve prosthesis is used as a cardiac valve prosthesis in the aorta, it is possible to mount it in three positions, viz., in the descending part of the aorta in a position between the coronary arteries and the left ventricle of the heart, or in the aorta in a position immediately after the mouth of the coronary arteries.

The cardiac valve prosthesis can also be used in other places than in the aorta. Thus, the valve prosthesis can be used in the pulmonary artery and/or the right ventricle of the heart for replacing the pulmonary valves. Likewise, the cardiac valve prosthesis can be used in the passage between the right auricle of the heart and the right ventricle of the heart (tricuspidalostium) and the passage between the left auricle of the heart and the left ventricle of the heart (mistralostium) for replacing the tricuspidal valve and the mitral valve, respectively.

Even though the cardiac valve preferably is meant to be used for patients suffering from aorta insufficiency and who cannot be offered an open heart surgery, the valve prosthesis can also be used for patents in connection with treatment of aorta stenosis. Several of the patients with aorta stenosis are elderly people who cannot be offered a surgical cardiac operation. The patients are offered balloon dilatation of the aorta stenosis which may result in an aorta insufficiency as a side effect of the treatment.

As to these patients it is possible to insert a valve prosthesis in the descending or ascending part of the aorta thoracalis a few days or weeks before the balloon dilatation. As a result thereof, the left ventricle is protected against weight if the subsequent balloon dilatation of the stenosis results in aorta insufficiency. In certain cases the weight (reflux) on the left ventricle is reduced by up to approximately 75%.

Furthermore, the stent may be made with a relatively great height and with a cylinder surface which is closed by a suitable material. Thus, a vascular prosthesis known per se is formed wherein the valve is mounted. This may facilitate the implantation of the valve prosthesis, for instance in the arcus aorta. Moreover, the great surface which abuts the inner wall of the channel contributes to ensure the securing of the valve prosthesis in the channel. This embodiment is also suitable as valve prosthesis which is inserted in veins. As veins have relatively thin and weaker walls than arteries, it is desirable that the valve prosthesis has a greater surface to distribute the outward pressure which is necessary to secure the valve prosthesis.

Moreover, the invention relates to a balloon catheter for implanting a valve prosthesis according to the invention and comprising a channel for injection of a fluid for the inflation of the balloon means of the catheter and an insertion cap wherein the balloon means of the catheter and a collapsible valve prosthesis mounted thereon are located during the injection, characterized in that the balloon means are provided with profiled surface which is made to ensure a steady fastening of the valve prosthesis during the withdrawal of the balloon means from the protection cap and the subsequent inflation for the expansion of the stent.

Different balloon catheters for implanting cores in the body are known. For instance. such balloon catheters are known from U.S. Pat. Nos. 4,856,516, 4,733,665 and 4,796,629 and from DE publication No. 2,246,526. However, the known balloon catheters have a smooth or a slightly wavy surface. The use of such balloon catheter is disadvantageous for mounting a valve prosthesis in a channel having a large flow as for instance the aorta. A large humour flow is able to displace the stent on the smooth surface of the balloon and makes an accurate positioning difficult. This drawback has been remedied with the balloon catheter according to the present invention as the profiled surface prevents a displacement of the valve prosthesis in relation to the balloon means during introduction and the subsequent inflation of the balloon means.

In connection with the implantation, any prior art technique may be used to supervise an accurate introduction and positioning of the valve prosthesis. Thus, guide wires for the catheter, X-ray supervision, injection of X-ray traceable liquids, ultrasonic measuring, etc. may be used.

DESCRIPTION OF THE DRAWINGS

The invention will now be explained in detail with reference to the accompanying schematical drawing, wherein FIGS. 8–10 are views illustrating three possible positions of a cardiac valve prosthesis.

DETAILED DESCRIPTION OF THE PREFERRED EMBODIMENTS

Figure 1:
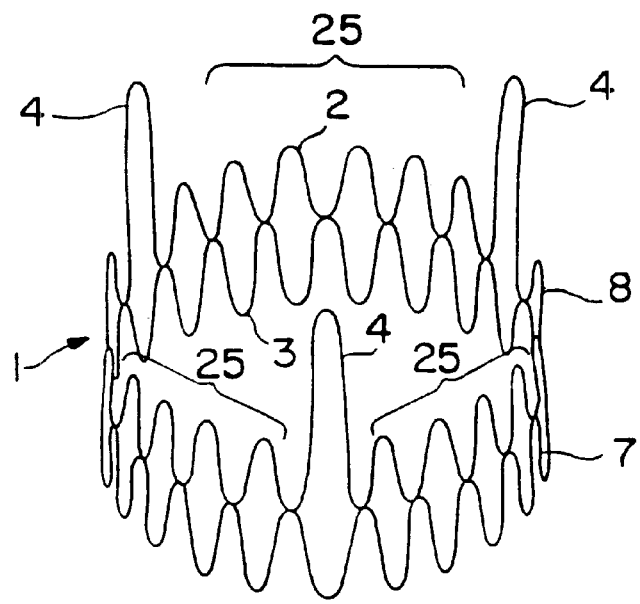
FIG. 1 shows a perspective view of a stent without a valve.
Figure 2:
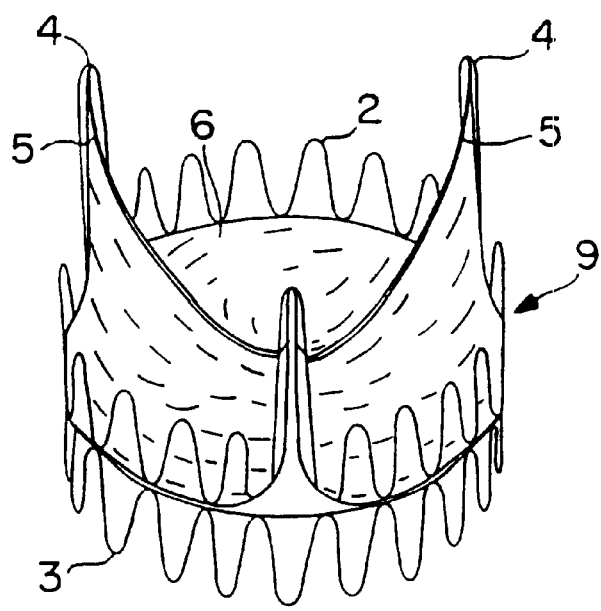
FIG. 2 is a perspective view of a valve prosthesis according to the invention made from the stent shown in FIG. 1 having a biological valve mounted thereon.

FIG. 1 shows a stent 1 made by support means in the form of two 0.55 mm surgical stainless steel wires 2,3. The wires are folded in 15 loops. Three loops 4 are 14 mm in height and are intended to secure the commissural points 5 (see FIG. 2) from a biological cardiac valve 6 which is mounted in the stent 1. The remaining loops have a height of 8 mm. These loops form circumferentially expandable sections 25 between the commissural points 5 forming commissural supports. Each of the two folded wires 2,3 is bent to form rings 7,8 which are closed by welding the ends. The two rings are placed on top of each other as will appear from FIG. 1 and they are mutually secured by means of a number of sutures (not shown). The lower ring is circumferentially expandable at least along sections thereof which correspond to the circumferentially expandable sections 25. By using a substantially cylindrical thread structure with projecting apices. a reduction in weight is obtained as compared to a stent which is exclusively cylindrical with the same loop heights for all the loops.

The biological valve 6 was removed from a slaughtered pig of 100 kg. The valve was cleaned before mounting in the stent 1. The cleaned valve has an outer diameter of 25–27 mm and the height of the three commissural points 5 is 8 mm. The valve 6 is mounted in the stent by means of a suitable number of sutures to form the cardiac valve prosthesis 9 shown in FIG. 2. The valve prosthesis produced is used for performing tests in pigs by implantation of cardiac valve prosthesis. However, the cardiac valve prosthesis for use in human beings has a corresponding form.

Figure 3:
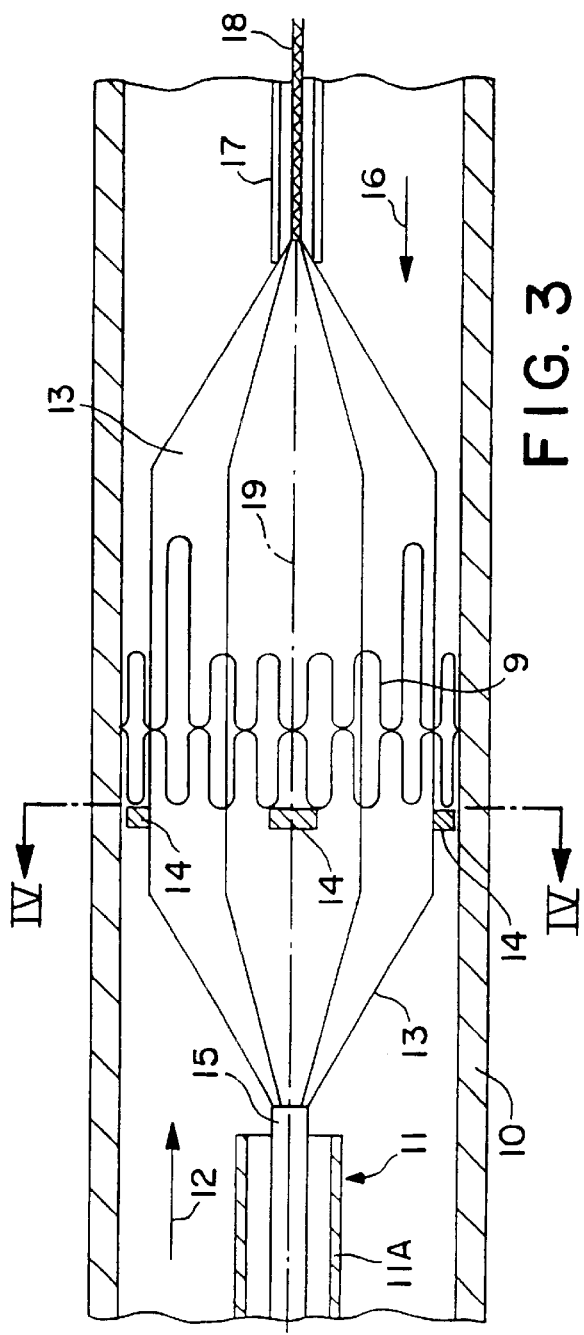
FIG. 3 is a partial view through the aorta illustrating a partially inflated balloon catheter.

FIG. 3 shows a partial view through the aorta 10. A balloon catheter 11 is introduced in the aorta according to the direction of an arrow 12. In the Figure shown the balloon means 13 of the balloon catheter is led out of the protection cap 11A and is partly inflated through a fluid channel 15, which is led to the surface of the patient. The balloon means 13 constitutes a tri-sectional balloon upon which the cardiac valve prosthesis is placed. In the form shown, the cardiac valve prosthesis is expanded exactly to be in contact with the aorta 10. The balloon means 13 is provided with three projecting beads 14 which are engaged with the one side of the cardiac valve prosthesis 9. The blood flowing through the aorta according to the direction of an arrow 16 will thus cause the cardiac valve prosthesis 9 to abut on the beads 14 and the valve cannot be displaced in relation to the balloon means 13. Moreover, the balloon catheter used comprises a central channel 17 to receive a guide wire 18 which is used in a way known per se for supervising the introduction of the catheter through fluoroscopi. In the shown embodiment beads 14 are only used at one side of the valve prosthesis, but, however, it will often be desirable to use the beads in pairs placed along lines parallel to the longitudinal axes 19 through the balloon means 13. In this case the spacing of the pair of beads 14 will correspond to the height of the loops of the stent. This makes it possible to make an effective fastening of a valve prosthesis on balloon means. Moreover, the fastening on the balloon means may be provided by using balloon means with an indentation in the surface (not shown).

Figure 4:
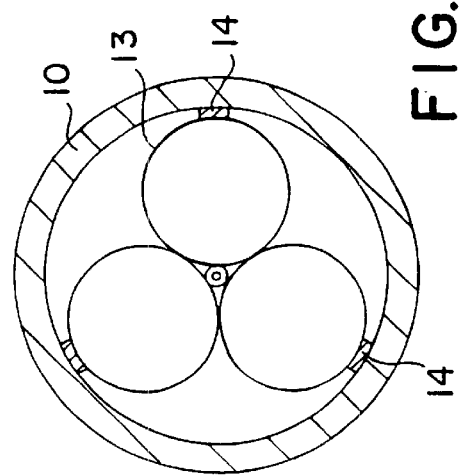
FIG. 4 is a cross section through the embodiment shown in FIG. 9, FIGS. 5–7 are views illustrating the introduction and implantation of a valve prosthesis of the invention in the aorta.

FIG. 4 shows a cross section through the embodiment shown in FIG. 3 illustrating the placing of the beads 14 on the tri-sectional balloon means 13.

A balloon catheter of the above-described type which was used in tests of implanting of cardiac valve prosthesis 9 in pigs had the following dimensions. Each of the three balloons was 60 mm in length and 15 mm in diameter. The total diameter for the three inflated balloons was 31 mm and in the balloon catheter used two beads 14 having a height of 3 mm were mounted on each side of the three balloons. The beads had a spacing of 15 mm. The protection cap 11A of the balloon catheter had an outer diameter of 13.6 mm and an inner diameter of 12.5 mm and a length of 75 cm. The balloon catheter was provided with a standard guide wire having a diameter of 0.9 mm and a length 300 cm.

FIGS. 5–7 show the valve prosthesis 9 at different steps in introducing and implanting in the aorta 10 by means of the catheter 11 having the inflatable balloon means 13. The cardiac valve prosthesis 9 is initially placed above the deflated balloon means 13 and compressed manually around the balloon means (FIG. 5), whereafter the outer diameter for the valve prosthesis is approximately 10 mm. After the introduction and positioning, the balloon means 13 is inflated (FIG. 6), thereby contributing an outer dimension of approximately 30 mm to the cardiac valve prosthesis. To obtain an effective fastening in the aorta, the outer dimension of the cardiac valve prosthesis is greater than the diameter of the aorta. This means that the prosthesis is tight against the inner wall of the aorta with a pressure which is sufficiently large to counteract a detachment due to the flow of the blood. The balloon catheter 11 may subsequently be removed from the aorta 10 (FIG. 7). Due to the stiffness of the metal the valve prosthesis will prevent a contraction. However, smaller contractions may occur (<10% diameter reduction) after the deflation and removal of the balloon catheter 13. When the valve prosthesis is mounted as shown in FIG. 7, the patient will be able to resume a substantially normal life after a few days.

FIGS. 8–10 show the positioning of the valve prosthesis 9 as cardiac valve prosthesis in the aorta 10 in three different positions, i.e., in a position between the coronary arteries 20 and the left ventricle of the heart 21 (FIG. 8), in a position immediately after the mouth of the coronary arteries in the ascending part of the aorta (FIG. 9), and in a position in the descending part of the aorta 10. The positioning of the valve prosthesis is chosen in accordance with the diagnosis of the illness of the patient. By placing the cardiac valve prosthesis as shown in FIG. 8, there is a risk of detachment and/or covering the mouth of the coronary arteries, and therefore it is preferred to use a higher stent which, for instance, comprises several ranges placed on top of each other. This allows a fixation of the prosthesis at a place after the mouth of coronary arteries even though the valve itself is in the position between the coronary arteries and the left ventricle. FIGS. 8 and 9 show how a contrast medium 23 is injected by means of a so-called pigtail catheter for registration of tightness of the implanted valve prosthesis 9.

A specific embodiment for a valve prosthesis and a balloon catheter for implanting the valve prosthesis has been explained above. However, it is obvious that it is possible to modify the valve prosthesis depending on the desired use, and moreover, it is possible to modify the catheter used in the implantation. Thus, the stent of the valve prosthesis may be made solely of one closed ring folded in a number of loops or with three or more mutually secured loop-shaped rings placed on top of each other. Moreover, it is possible to make the stent having a thread structure which instead of loops is grate shaped, helical or is formed otherwise if only it is ensured that the form of the stent permits the compression and expansion of the stent and fastening of the collapsible valve. Instead of a biological valve it might be possible to use other collapsible valves, such as valves made from synthetic materials, e.g., polyurethane. It is also possible to use valves with more or fewer flaps than three.

Figure 11:
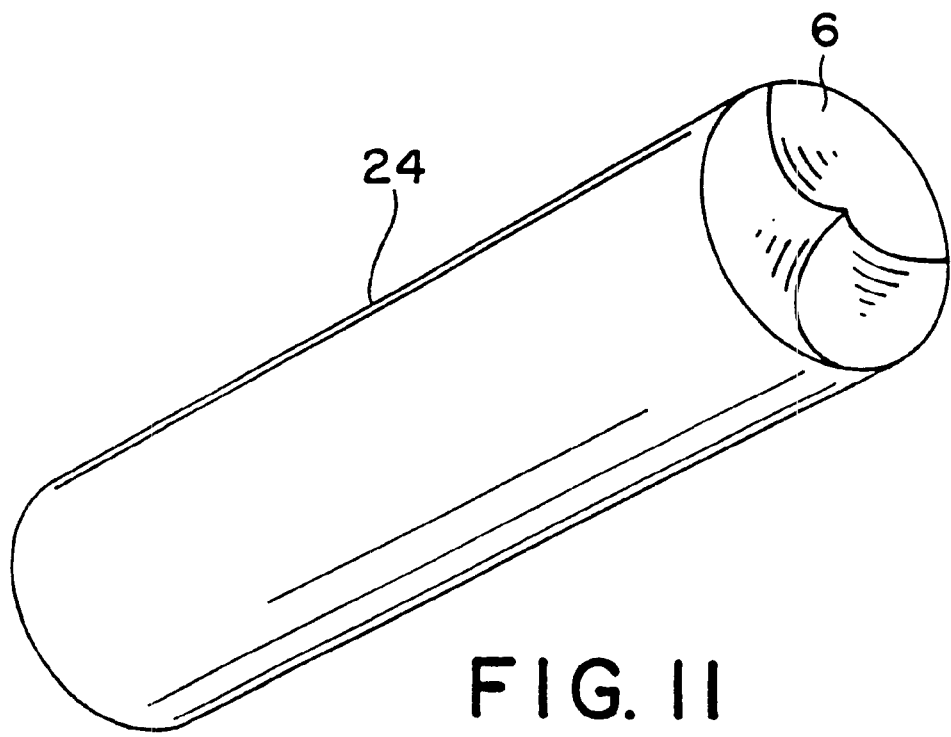
FIGS. 11–12 are perspective views illustrating two further embodiments of a valve prosthesis having a closed cylindrical wall.
Figure 12:
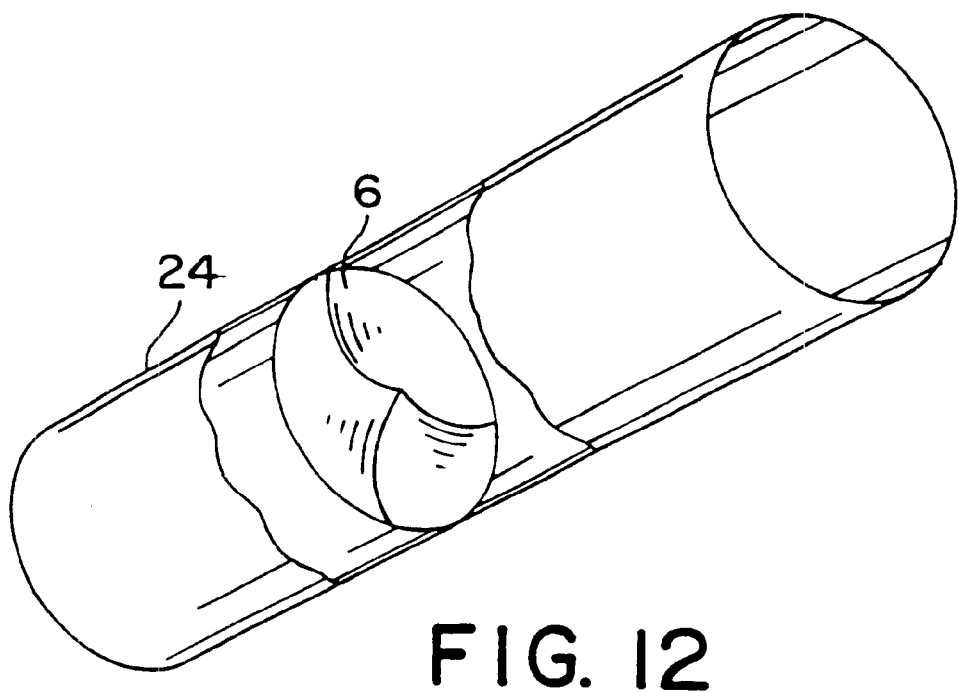

It is possible to make the valve prosthesis with a closed cylinder surface as illustrated in FIGS. 11 and 12. In both Figures the support means of the valve prosthesis is made of an elongated tubular means 24 having a closed cylinder surface. This valve prosthesis is intended to expand by self-expansion or by means of a catheter according to the invention. This prosthesis is especially suitable for placing in veins and other channels where only a small pressure is exerted against the wall of the channel. In FIG. 11 the valve 6 is mounted at the end of the tubular means 24. In FIG. 12 an embodiment is shown where the valve 6 is mounted in a central position in the tubular means 24.

An explanation of a method of implanting a valve prosthesis according to the invention is given below:

- a valve prosthesis 9 made of a stent 1 and a collapsible valve 6, as described above, is placed on a deflated balloon means and is manually compressed thereon,
- the balloon means 13 and the valve prosthesis are drawn into an insertion cover 11A,
- a guide wire 18 is inserted into the left ventricle of the heart through the central opening 17 of the balloon catheter under continuous fluoroscopi,
- the insertion cover 11A conveys the guide wire 18 to a point in the channel in the immediate vicinity of the desired position of the valve prosthesis,
- the balloon means 13 is pushed out of the protection cap 11A and the valve prosthesis is positioned in the desired position if necessary by use of further registration means to ensure an accurate positioning,
- the balloon means 13 is inflated with a certain overstretching of the channel,
- the balloon means 13 is deflated, and
- the balloon means 13, the guide wire 18 and the protection cap 11A are drawn out and the opening in the channel, if any, wherein the valve prosthesis is inserted can be closed.

What is claimed is:

1. A valve prosthesis for implantation in a body channel having an inner wall, the prosthesis comprising;
   a radially collapsible and expandable cylindrical stent, the stent including a cylindrical support means having a cylinder surface; and
   a collapsible and expandable valve having commissural points, the valve mounted to the stent at the commissural points, wherein the stent and valve are configured to be implanted in the body by way of catheterization.

2. The valve prosthesis according to claim 1, wherein the support means is made of thread structure.

3. The valve prosthesis according to claim 2, wherein the thread structure comprises several spaced apices that extend from one end of the cylindrical support means in a direction along a longitudinal axis of the cylindrical support means, the commissural points of the valve being attached to the apices.

4. The valve prosthesis according to claim 3, wherein the collapsible valve is a biologically trilobate valve.

5. The valve prosthesis according to claim 1, wherein the stent comprises at least two closed rings, each formed from more than three loops, the rings connected one to another, and wherein three of the loops in at least one of the rings has a greater height than the remaining loops.

6. The valve prosthesis according to claim 5, wherein each of the rings of the stent is made from a wire having a diameter of 0.05 mm and a loop height of approximately 8 mm and approximately 14 mm for the three greater height loops, and that the cylindrical wire structure produced and the collapsible valve mounted thereon in a folded state have an outer diameter of approximately 10 mm and in an expanded state an outer diameter of approximately 30 mm.

7. The valve prosthesis according to claim 5, wherein three or more mutually attached rings placed on top of each other are used in that the stent is made to be fixed through the expansion at one point in the channel where the valve prosthesis is inserted, which point is different from the point where the valve is mounted in the stent.

8. The valve prosthesis according to claim 1, wherein the cylinder surface of the support means is closed to form a tubular element.

* * * * *

(12) EX PARTE REEXAMINATION CERTIFICATE (8469th)
United States Patent
Andersen et al.

(10) Number: US 6,582,462 C1
(45) Certificate Issued: Aug. 16, 2011

(54) VALVE PROSTHESIS FOR IMPLANTATION IN THE BODY AND A CATHETER FOR IMPLANTING SUCH VALVE PROSTHESIS

(75) Inventors: Henning Rud Andersen, Hoejbjerg (DK); John Michael Hasenkam, Aarhus V (DK); Lars Lyhne Knudsen, Aarhus C (DK)

(73) Assignee: Edwards Lifesciences AG, St.-Prex (CH)

Reexamination Request:
No. 90/009,791, Jul. 29, 2010

Reexamination Certificate for:
Patent No.: 6,582,462
Issued: Jun. 24, 2003
Appl. No.: 09/514,426
Filed: Feb. 28, 2000

Related U.S. Application Data

(60) Continuation of application No. 09/026,574, filed on Feb. 20, 1998, now Pat. No. 6,168,614, which is a continuation of application No. 08/955,228, filed on Oct. 21, 1997, now abandoned, which is a division of application No. 08/801,036, filed on Feb. 19, 1997, now Pat. No. 5,840,081, which is a continuation of application No. 08/352,127, filed on Dec. 1, 1994, now abandoned, which is a division of application No. 08/261,235, filed on Jun. 14, 1994, now Pat. No. 5,411,552.

(51) Int. Cl.
*A61F 2/24* (2006.01)

(52) U.S. Cl. ............................ 623/1.26; 623/2.14
(58) Field of Classification Search .................. None
See application file for complete search history.

(56) References Cited

U.S. PATENT DOCUMENTS

| | | |
|---|---|---|
| 3,275,211 A | 9/1966 | Hirsch et al. |
| 3,409,013 A | 11/1968 | Berry |
| 3,472,230 A | 10/1969 | Forgarty et al. |
| 3,548,417 A | 12/1970 | Kisher |
| 3,657,744 A | 4/1972 | Ersek |
| 3,671,979 A | 6/1972 | Moulopoulos |
| 3,755,823 A | 9/1973 | Hancock |
| 3,868,956 A | 3/1975 | Alfidi et al. |
| 4,056,854 A | 11/1977 | Boretos et al. |
| 4,345,340 A | 8/1982 | Rosen |
| 4,373,216 A | 2/1983 | Klawitter |
| 4,406,022 A | 9/1983 | Roy |
| 4,535,483 A | 8/1985 | Klawitter et al. |
| 4,605,407 A | 8/1986 | Black et al. |
| 4,643,732 A | 2/1987 | Pietsch et al. |

(Continued)

FOREIGN PATENT DOCUMENTS

| | | |
|---|---|---|
| DE | 2246526 | 9/1972 |
| DE | E 60 500 B | 11/1986 |
| DE | 36 40 745 A1 | 11/1986 |
| DE | 691 13 818 T2 | 5/1991 |
| DK | 1246/90 | 7/1968 |

(Continued)

OTHER PUBLICATIONS

First Expert Report of Professor John R. Pepper in German High Court of Justice Chancery Division Patents Court, HC07 CO1243 signed Apr. 28, 2008.
Exhibit JRP–1 referred to in the First Expert report of Professor John R. Pepper in German High Court of Justice Chancery Division Patents Court, HC07 CO1243 signed Apr. 28, 2008.

(Continued)

*Primary Examiner* — Cary Wehner

(57) ABSTRACT

A valve prosthesis for implantation in the body by use of a catheter includes a stent made from an expandable cylinder-shaped thread structure having several spaced apices. The elastically collapsible valve is mounted on the stent as the commissural points of the valve are secured to the projecting apices.

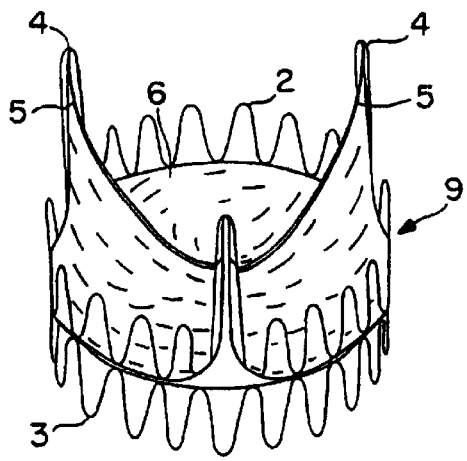

U.S. PATENT DOCUMENTS

| | | | |
|---|---|---|---|
| 4,687,483 | A | 8/1987 | Fisher et al. |
| 4,759,758 | A | 7/1988 | Gabbay |
| 4,762,128 | A | 8/1988 | Rosenbluth |
| 4,796,629 | A | 1/1989 | Grayzel |
| 4,829,990 | A | 5/1989 | Thuroff et al. |
| 4,851,001 | A | 7/1989 | Taheri |
| 4,878,906 | A | 11/1989 | Lindemann et al. |
| 4,913,141 | A | 4/1990 | Hillstead |
| 4,922,905 | A | 5/1990 | Strecker |
| 5,080,668 | A | 1/1992 | Bolz et al. |
| 5,135,536 | A | 8/1992 | Hillstead |
| 5,266,073 | A | 11/1993 | Wall |
| 5,411,552 | A | 5/1995 | Andersen et al. |
| 5,607,471 | A | 3/1997 | Seguin et al. |
| 5,840,081 | A | 11/1998 | Andersen et al. |
| 6,098,481 | A | 8/2000 | Mills et al. |
| 6,461,366 | B1 | 10/2002 | Seguin et al. |
| 6,562,058 | B2 | 5/2003 | Seguin et al. |
| 6,618,614 | B1 | 9/2003 | Chance |
| 6,689,164 | B1 | 2/2004 | Seguin et al. |
| 7,018,406 | B2 | 3/2006 | Seguin et al. |
| 7,252,682 | B2 | 8/2007 | Seguin |
| 7,344,556 | B2 | 3/2008 | Seguin et al. |
| 2010/0286769 | A1 | 11/2010 | Andersen et al. |

FOREIGN PATENT DOCUMENTS

| | | |
|---|---|---|
| EP | 0 221 570 | 11/1986 |
| EP | 0 292 587 | 5/1987 |
| EP | 0 592 410 B1 | 10/1995 |
| GB | 1 268 484 | 6/1969 |
| GB | 2 056 023 A | 3/1981 |
| GB | 2 056 023 A | 8/1997 |
| SU | 158 988 | of 1963 |
| SU | 1371700 | 2/1988 |
| SU | 1457921 | 2/1989 |
| WO | WO 83/03752 | 11/1983 |
| WO | 91/17720 | 11/1991 |
| WO | WO 2006/127765 A1 | 11/2006 |

OTHER PUBLICATIONS

Exhibit JRP-2 referred to in the First Expert report of Professor John R. Pepper in German High Court of Justice Chancery Division Patents Court, HC07 CO1243 signed Apr. 28, 2008.

Exhibit JRP-3 referred to in the First Expert report of Professor John R. Pepper in German High Court of Justice Chancery Division Patents Court, HC07 CO1243 signed Apr. 28, 2008.

Exhibit JRP-4 referred to in the First Expert report of Professor John R. Pepper in German High Court of Justice Chancery Division Patents Court, HC07 CO1243 signed Apr. 28, 2008.

Exhibit JRP-5 referred to in the First Expert report of Professor John R. Pepper in German High Court of Justice Chancery Division Patents Court, HC07 CO1243 signed Apr. 28, 2008.

Exhibit JRP-6 referred to in the First Expert report of Professor John R. Pepper in German High Court of Justice Chancery Division Patents Court, HC07 CO1243 signed Apr. 28, 2008.

Exhibit JRP-7 referred to in the First Expert report of Professor John R. Pepper in German High Court of Justice Chancery Division Patents Court, HC07 CO1243 signed Apr. 28, 2008.

Second Expert Report of Professor John R. Pepper in German High Court of Justice Chancery Division Patents Court, HC07 CO1243 signed Jun. 20, 2008.

First Expert Report of Dr. Anthony C. Lunn in German High Court of Justice Chancery Division Patents Court, HC07 CO1243 signed May 4, 2008.

Exhibit ACL 1 referred to in the First Expert Report of Dr. Anthony C. Lunn in German High Court of Justice Chancery Division Patents Court, HC07 CO1243 signed Mar. 24, 2008.

Affidavit by Dr. Anthony C. Lunn, ACL Consulting LLC, 47 Hawthorne Avenue, Princeton, NJ 08540 signed Feb. 13, 2009.

Expert Report of Professor Martin Terry Rothman in German High Court of Justice Chancery Division Patents Court, HC07 CO1243 dated Apr. 28, 2008 and signed Jun. 9, 2008.

Reply Expert Report of Professor Martin Terry Rothman in German High Court of Justice Chancery Division Patents Court, HC07 CO1243 dated May 27, 2008 and signed Jun. 9, 2008.

Curriculum Vitae of Martin Terry Rothman.

Reply Expert Report of Professor Richard A. Hillstead in German High Court of Justice Chancery Division Patents Court, HC07 CO1243 dated May 27, 2008 and signed May 27, 2008.

Exhibit RAH 14 referred to in the Reply Expert Report of Richard A. Hillstead dated May 27, 2007.

First Expert Report of Dr. Nigel Pearson Buller in German High Court of Justice Chancery Division Patents Court, HC07 C01243 dated Apr. 28, 2008 and signed Apr. 28, 2008.

Exhibit NPB–1 referred to in the First Expert Report of Dr. Nigel Pearson Buller in German High Court of Justice Chancery Division Patents Court, HC07 C01243 dated Apr. 28, 2008.

Exhibit NPB–2 referred to in the First Expert Report of Dr. Nigel Pearson Buller in German High Court of Justice Chancery Division Patents Court, HC07 C01243 dated Apr. 28, 2008.

Exhibit NPB–3 referred to in the First Expert Report of Dr. Nigel Pearson Buller in German High Court of Justice Chancery Division Patents Court, HC 07 C01243 dated Apr. 28, 2008.

Exhibit NPB–4 referred to in the First Expert Report of Dr. Nigel Pearson Buller in German High Court of Justice Chancery Division Patents Court, HC 07 C01243 dated Apr. 28, 2008.

Exhibit NPB–5 referred to in the First Expert Report of Dr. Nigel Pearson Buller in German High Court of Justice Chancery Division Patents Court, HC 07 C01243 dated Apr. 28, 2008.

Exhibit NPB–6 referred to in the First Expert Report of Dr. Nigel Pearson Buller in German High Court of Justice Chancery Division Patents Court, HC 07 C01243 dated Apr. 28, 2008.

Exhibit NPB–7 referred to in the First Expert Report of Dr. Nigel Pearson Buller in German High Court of Justice Chancery Division Patents Court, HC 07 C01243 dated Apr. 28, 2008.

Exhibit NPB–8 referred to in the First Expert Report of Dr. Nigel Pearson Buller in German High Court of Justice Chancery Division Patents Court, HC 07 C01243 dated Apr. 28, 2008.

Second Expert Report of Dr. Nigel Pearson Buller in German High Court of Justice Chancery Division Patents Court, HC 07 C01243 dated May. 27, 2008 and signed Jun. 18, 2008..
Exhibit NPB–9 referred to in the Second Expert Report of Dr. Nigel Pearson Buller in German High Court of Justice Chancery Division Patents Court, HC 07 C01243 dated May 27, 2008.
Exhibit NPB–10 referred to in the Second Expert Report of Dr. Nigel Pearson Buller in German High Court of Justice Chancery Division Patents Court, HC 07 C01243 dated May 27, 2008.
Handbook of Coronary Stents, Martin Dunitz Ltd. 1997, pp. 1–10, Exhibit D13 in Nullity Proceedings *Corevalvev. Edwards*.
Textbook of Interventional Cardiology, W.B. Saunders Company, 1990, pp. 2–21, Exhibit D14 in Nullity Proceedings *Corevalvev. Edwards*.
Ballon Aortic Valbuloplasty, Brice Letac and Alain Cribier, pp. 239–253, Exhibit D14 in Nullity Proceedings *Corevalvev. Edwards*.
Balloon Expandable Stent Implantation in Stenoic Right Heart Valved Conduits, JACC vol. 16, No. 5, Nov. 1, 1990, pp. 1310–1314, Exhibit D16 in Nullity Proceedings *Corevalvev. Edwards*.
Perkutane Implantation von Gefabendoprothesen (Stents) in Becken–und Oberschenkelarterien, DMW 1989, 114, Jg., Nr. 40 pp. 1517–1523, Exhibit D17 in Nullity Proceedings *Corevalvev. Edwards*.
Normal and Stenotic Renal Arteries: Experimental Balloon–expandable Intraluminal Stenting, Radiology, Sep. 1987, pp. 708–708, Exhibit D18 in Nullity Proceedings *Corevalvev. Edwards*.
The New England Journal of Medicine, vol. 916, No. 12, Mar. 19, 1987, Exhibit D19 in Nullity Proceedings *Corevalvev. Edwards*.
Expandable intramural vascular graft: A feasibility study, Surgery, vol. 99, No. 2, Feb. 1986, pp. 199–205, Exhibit D20 in Nullity Proceedings *Corevalvev. Edwards*.
Perkutan implantierbare, durch Ballon aufdehnbare Gefaprothese, DMW 1988, 113, Jg., Nr. 14, pp. 538–542, Exhibit D21 in Nullity Proceedings *Corevalvev. Edwards*.
Investigative Radiologhy, Transluminally–placed Coilspring Endarterial Tube Grafts, Charles T. Doiter, MD, Sep.–Oct. 1969, vol. 4, pp. 329–332, Exhibit D22 in Nullity Proceedings *Corevalvev. Edwards*.
Perspective, Peripheral Angioplasty and the Newer Circulatory Interventiosn: Whose Responsibility?, AJR 150, Jun. 1988, pp. 1236–1239, Exhibit D23 in Nullity Proceedings *Corevalvev. Edwards*.
Circulation Journal of the American Heart Association, Percutaneous Aortic Valve Implantation Retrograde From the Femoral Artery, Feb. 14, 2006; 113; pp. 842–850.
Interventional Cardiac Catheterization at Duke Medical Center, The American Journal of Cardiology, Oct. 1, 1988, vol. 62.
The New England Journal of Medicine, vol. 316, Mar. 19, 1987, No. 12, Intravasuclar Stents to Prevent Occlusion and Restenosis After Transluminal Angioplasty.
Laboratory Investigation, Intra–Arterial Stenting in the Atherosclerotic Rabbit, pp. 646–653 with Investigations Concerning the Flexible Coil Stent.
Laboratory Investigation, Early and later results of intracoronary arterial stenting after coronary angioplasty in dogs, vol. 76, No. 4, Oct. 1987, pp. 891–897 with Intracoronary Stenting for Acute Closure Following Percutaneous Transluminal Coronary Angioplasty; Intraluminal Stenting of Iliac Artery Stenosis: Preliminary Report of a Multicenter Trial; Balloon Expandable Intravascular Stents in Human Coronary Arteries: Report of Initial Experience; Reexpansion of Aortic Balloon Expandable Stents Following Growth in Juvenile Swine.
Progress in Radiology, Balloon–Expandable Intravascular Stent, AJR 150, Jun. 1988, pp. 1263–1269.
Intervention, Intravascular Stents for Angioplasty, Reprinted with permission from Cardio, Dec. 1987.
Reprinted from Radiology, vol. 164, No. 3, pp. 705–708, Normal and Stenotic Renal Arteries: Experimental Balloon—expandable Intraluminal Stenting with Report of a New Articulated Balloon Expandable Intravascular Stent; Report of a New Radiopaque Balloon Expandable Intravascular Stent in Canine Coronary Arteries; Balloon Expandable Stent Implantation in Stenotic Right Heart Valved Conduits; Stent Implantation in Vein Grafts: Safety, Patency, and Host Response.
Historical Overview, pp. 1–16.
Cath Lab Digest, Percutaneous Aortic Valve Replacement, Apr. 24, 2008, pp. 1–5.
Edwards Lifesciences, Edwards Lifesciences Announces First Human Implants of Next–Generation Transcatheter Heart Valve, pp. 1–2.
CoreValve, News Release, CoreValve announces that more than 500 high–risk patients have been treated with its ReValving System for percutaneous aortic valve replacement (PAVR).
Catheterization and Cardiovascular Interventions 68: 199–204 (2006), Rapid Pacing to Facilitate Transcatheter Prosthetic Heart Valve Implantation.
Journal of the American College of Cardiology, vol. 50, No. 1, pp. 69–76, Jul. 3, 2007, Percutaneous Aortic Valve Replacement for Severe Aortic Stenosis in High–Risk Patients Using the Second–and Current Third–Generation Self–Expanding CoreValve Prosthesis.
Second International Congress on: Laser and Stent Therapy in Vascular Disease–Scottsdale, Arizona, Corporate Research Trip Report, Rick Hillstead, Feb. 27, 1989, pp. 1–8.
Laser and Stent Therapy In Vascular Surgery, International Congress II, Feb. 10–15, 1989, Scottsdale, Arizona.
A View of Vascular Stents, Richard A. Schatz, MD, pp. 445–457.
Corporate Research Report, A Brief History and Report on Current Clinical Experiences with: Intravascular Stenting in Coronary and peripheral Applications: A Potential New Treatment for the Prevention of Restenosis and Abrupt Closure After Balloon Angioplasty, Rick Hillstead, Apr. 3, 1989.
Radiology, Apr. 1990, Flexible Tantalum Stents Implanted in Aortas and Iliac Arteries: Effects in Nornal Canines, pp. 91–96.
International Congress (III), Lasers, Stents and Interventions in Vascular Disease, Feb. 11–16, 1990, Scottsdale, Arizona.
Letter Vossius & Partner (in German) (Cited as Ex. K3 in Nullity Proceedings *CoreValvev. Edwards*.
European Heart Journal, 1992 13, pp. 704–708, Transmittal implantation of artificial heart valves. (Cited as Ex. K4 in Nullity Proceedings *CoreValvev. Edwards*).

Expert Report of Professor Martin Terry Rothman (Cited as Ex. K5 in Nullity Proceedings *CoreValve*v. *Edwards*).
Translation of Expert Report of Professor Martin Terry Rothman (Cited as Ex. K5a in Nullity Proceedings *CoreValve*v. *Edwards*).
Expert Report of Richard A. Hillstead (Cited as Ex. K6 in Nullity Proceedings *CoreValve*v. *Edwards*).
Translation of Expert Report of Richard A. Hillstead (Cited as Ex. K6a in Nullity Proceedings *CoreValve*v. *Edwards*).
Translation of Expert Report of Dr. Nigel Pearson Buller (Cited as Ex. K7 in Nullity Proceedings *CoreValve*v. *Edwards*).
First Expert Report of Dr. Nigel Pearson Buller (Cited as Ex. K7a in Nullity Proceedings *CoreValve*v. *Edwards*).
Boards of Appeal of the European Patent Office, Case No. T0123/06 –3.3.10 (Cited as Ex. K8 in Nullity Proceedings *CoreValve*v. *Edwards*).
Exclusive License Agreement between Stanford Surgical Technologies, Inc. and H.R. Andersen, J.M. Hasankam, L.L. Knudsen marked Exhibit A with Exhibits B, C. D (Cited as Ex. K9 in Nullity Proceedings *CoreValve*v. *Edwards*).
Assignment and License Agreement between H.R. Andersen, J.M. Hasankam, L.L. Knudsen and Edwards Lifesciences (Cited as Ex. K10 in Nullity Proceedings *CoreValve*v. *Edwards*).
First Expert Report of Professor John R. Pepper (Cited as Ex. K11 in Nullity Proceedings *CoreValve*v. *Edwards*).
Translation of First Expert Report of Professor John R. Pepper (Cited as Ex. K11a in Nullity Proceedings *CoreValve*v. *Edwards*).
CoreValve News Release of Nov. 30, 2006 (Cited as Ex. K13 in Nullity Proceedings *CoreValve*v. *Edwards*).
Erklarung von Drs. U. Schafer and F. Hartmenn (Cited as Ex. K14 in Nullity Proceedings *CoreValve*v. *Edwards*).
Erklarung von Dr. R. Lange (Cited as Ex. K15 in Nullity Proceedings *CoreValve*v. *Edwards*).
Letter addressed to Prof. Dr. Jacques Seguin, MD PhD, dated Apr. 5, 2008 (in German) (Cited as Ex. K16 in Nullity Proceedings *CoreValve*v. *Edwards*).
Article (in German) entitled Neue Herzklappe ohne OP (possibly Cited as Ex. K17 in Nullity Proceedings *CoreValve*v. *Edwards*).
European Journal of Cardio–thoracic Surgery 32 (2007), pp. 291–294, Coronary Flow obstruction in percutaneous aortic valve replacement. (Cited as Ex. K18 in Nullity Proceedings *CoreValve*v. *Edwards*).
Lizensatze fur Technische Erfindungen of O. Hellebrand, G. Kaube, Dr. R. von Flackenstein (Cited as Ex. K19 in Nullity Proceedings *CoreValve*v. *Edwards*).
Urteil—Edwards Lifesciences PVT, Inc. and Edwards Lifesciences AG, dated Oct. 16, 2008 (Cited as Ex. K20 in Nullity Proceedings *CoreValve*v. *Edwards*).
Decision of the Technical Board of Appeal 3.2.2, dated Apr. 2, 1996 (Cited as Ex. K14 in Nullity Proceedings *CoreValve*v. *Edwards*).
Eidesstattliche Versicherug, dated Feb. 3, 2009, signed by R. Steiner (Cited as Ex. K23 in Nullity Proceedings *CoreValve*v. *Edwards*).
Correspondence (in German) from Reimann, Osterrieh, Kohler, Haft (Cited as Ex. K24 in Nullity Proceedings *CoreValve*v. *Edwards*).
Correspondence (in German) from Hoffmann–Eitle, dated May 29, 2009 (Cited as Ex. K25 in Nullity Proceedings *CoreValve*v.*Edwards*).
Patent Cooperation Treaty International Preliminary Examination Report (Cited as Ex. K26 in Nullity Proceedings *CoreValve*v. *Edwards*).
Correspondence (in German) from Hoffmann–Eitle, dated Jul. 20, 1992(Cited as Ex. K26a in Nullity Proceedings *CoreValve*v. *Edwards*).
Correspondence from Lehmann & Ree, dated Dec. 14, 1992(Cited as Ex. K27 in Nullity Proceedings *CoreValve*v. *Edwards*).
Correspondence (in German) from Hoffmann–Eitle, dated Dec. 14, 1992 (Cited as Ex. K27a in Nullity Proceedings *CoreValve*v. *Edwards*).
A Valve Prosthesis for Implantation in the Body and a Catheter for Implanting Such Valve Prosthesis. (Cited as Ex. K28 in Nullity Proceedings *CoreValve*v. *Edwards*).
Taschenbuch fur den Maschinebau (Cited as Ex. K29 in Nullity Proceedings *CoreValve*v. *Edwards*).
Delaware Secretary of State Certificate of Merger, dated Apr. 9, 2009 (Cited as Ex. K30 in Nullity Proceedings *CoreValve*v.*Edwards*).
Delaware Secretary of State Certificate of Conversion, dated Apr. 20, 2009 (Cited as Ex. K30/2 in Nullity Proceedings *CoreValve*v. *Edwards*).
Hoffman & Eitle handwritten in German notes (Cited as Ex. K31 in Nullity Proceedings *CoreValve*v. *Edwards*).
Drawing dated Jan. 19, 2010, Fig. 1B (Cited as Ex. K31 in Nullity Proceedings *CoreValve*v. *Edwards*).
Cardiovascular Medicine, May 2006, vol. 3, No. 5, pp. 256–264, Surgery Insight: current advances in percutaneous heart valve replacement and repair. (Cited as Ex. K32 in Nullity Proceedings *CoreValve*v. *Edwards*).
Convenience Translation to Federal Patent Court, dated Feb. 16, 2009.
Convenience Translation to Federal Patent Court, dated Feb. 16, 2009 from Vossius & Partner.
Convenience Translation to Federal Patent Court, dated Feb. 16, 2009 regarding Hearing Information.
Convenience Translation to Federal Patent Court, dated Jun. 20, 2007 from Vossius & Partner, regarding Nullity Action.
Correspondence from H.R. Andersen, M.D. to Rick Hillstead, dated Mar. 6, 1989.
European Heart Journal correspondence from D.L. Brutsaert, Basic Cardiology Editor, regarding manuscript submitted to European Heart Journal by H.R. Andersen, L.L. Knudsen and J.M. Hasenkam.
European Heart Journal correspondence from D.L. Brutsaert, Basic Cardiology Editor, dated Oct. 3, 1991, to Dr. Andersen regarding his paper Ms EHJ BC–109 is accepted for publication.
Circulation, University of California San Diego School of Medicine and UCSD Medical Center correspondence, dated Feb. 5, 1991, to H.R. Andersen, MD.
Indian Heart J 2007; Suppl B: B118–B132, Percutaneous Aortic Valves: Emerging.
Circulation, University of California San Diego School of Medicine and UCSD Medical Center correspondence, dated Oct. 9, 1990, to H.R. Andersen, MD.
Journal of the American College of Cardiology correspondence, dated Jul. 26, 1990, from Simon Dack, MD, Editor–in–Chief to R.H. Anderson, MD (marked DD235.001).
Journal of the American College of Cardiology correspondence, dated Jul. 26, 1990, from Simon Dack, MD, Editor–in–Chief to R.H. Anderson, MD (marked DD234.001).

Correspondence from Bird & Bird, dated Aug. 16, 2007, to Federal Patent Court, Complaint because of declaration of nullity of patent EP 0592 410 (DE 691 13 818).

Correspondence to Federal Patent Court, dated Jun. 2, 2008, Reasons for the opposition against the nullity action.

Convenience Translation to Federal Court, dated Jun. 10, 2008, from Bardehle, Pagenberg, Dost, Altenburg, Geisller.

Correspondence from Federal Patent Court, dated Aug. 14, 2008, to Bird & Bird, Summons to oral proceedings.

Correspondence from Federal Patent Court, dated Oct. 2, 2008, to Bird & Bird.

Correspondence to Federal Patent Court, dated Oct. 10, 2008, from Boehmert & Boehmert.

Correspondence to Federal Patent Court, dated Oct. 28, 2008.

Correspondence to Federal Patent Court, dated Nov. 17, 2008, Responsible to the communication from the Federal Patent Court of Oct. 2008 and the submissions of the plaintiff dated Aug. 4, 2008.

Correspondence to Federal Patent Court, dated Nov. 20, 2008, from Boehmert & Boehmert, Nullity proceedings regarding the German part of European Patent 592 410.

Federal Patent Court, Decision.

Correspondence to Federal Patent Court, dated Feb. 5, 2009, from Vossius & Partner.

Correspondence to Federal Patent Court, dated Feb. 11, 2009, Response to the submission by CoreValve dated Feb. 5, 2009.

Correspondence to Federal Patent Court, dated Dec. 24, 2009, from Hoffman–Eitle.

Correspondence to Federal Patent Court, dated Jan. 13, 2010, from Bird & Bird.

German Federal Patent Court, dated Jan. 19, 2010, Judgment.

Federal Patent Court, dated Jan. 19, 2010, Minutes.

Correspondence to Federal Patent Court, dated Mar. 22, 2010, from Hoffmann–Eitle.

Correspondence from Federal Patent Court to Bird & Bird LLP.

German Federal Patent Court, Decision Concerning The Correction.

Correspondence to German Federal Supreme Court, dated Jan. 12, 2011, from Hoffman–Eitle.

Correspondence to Federal Patent Court, dated Aug. 14, 2007, Litigating Intervention and Opposition.

Correspondence to The High Court of Justice, Chancery Division Patents Court, Re–Amended Defence and Counterclaim, from Bird & Bird.

Claim Form in the High Court of Justice, Chancery Division Royal Courts of Justice, Issue Date May 11, 2007.

Correspondence from the Supreme Court of the United Kingdom to Bird & Bird, dated Aug. 2, 2010, permission to appeal with a copy of application, information about the decision being appealed, copy of patent in suit (EP 0 592 410 B1).

High Court of Justice, Chancery Division Patents Court, dated Jan. 9, 2009, Judgment.

High Court of Justice, Chancery Division Patents Court, dated Mar. 28, 2008, Re–Re–Amended Grounds of Invalidity.

High Court of Justice, Chancery Division Patents Court, dated Mar. 28, 2008, Re–Re–Amended Particulars of Claim.

Correspondence to The High Court of Justice, Chancery Division Patents Court, dated Jun. 6, 2008 from Bird & Bird, Amended Particulars of Infringement.

High Court of Justice, Chancery Division Patents Court, dated Jun. 17, 2008, Amended Reply and Defence to Counterclaim.

File History for U.S. Patent No. 5,411,552 (Adensen et al) submitted as Plaintiff Trial Exhibit 3 in C.A. No. 08–091–GMS in the District Court of Delaware.

Danish Patent Application No. 1246/90 (Andersen et al.).

Instructions for use enclosed within PX 10 (CoreValve packaged device) submitted as Plaintiff Trial Exhibit 23 in C.A. No. 08–091–GMS in the District Court of Delaware.

Press Release: "CoreValve to be acquired Medtronic for $700 million—Medtronic targets leadership role in high-growth aortic transcatheter valves." submitted as Plaintiff Trial Exhibit 49 in C.A. No. 08–091–GMS in the District Court of Delaware.

Manuscript: Kappetein et al., Transapical Implantation of a Self–Expanding Aortic Valve Bioprosthesis—Animal Feasibility Study submitted as Plaintiff Trial Exhibit 56 in C.A. No. 08–091–GMS in the District Court of Delaware.

Photo of the Andersen Protoype Device from the Aarhus University webpage submitted as Plaintiff Trial Exhibit 82 in C.A. No. 08–091–GMS in the District Court of Delaware.

Press Release re: CoreValve Establishes U.S. Operations, Hires Veteran Medical Device Management and Development Team, submitted as Plaintiff Trial Exhibit 109 in C.A. No. 08–091–GMS in the District Court of Delaware.

CoreValve, Inc.'s Objections and Re Designated Responses to Interrogatory Nos. 1–7, & 9–13 of Plaintiffs' First Set of Interrogatories and Supplemental Responses to Interrogatory Nos. 9 and 13 submitted as Plaintiff Trial Exhibit 151 in C.A. No. 08–091–GMS in the District Court of Delaware.

Knudsen et al., Catheter—Implanted Hasenkam Hasenkam Prosthetic Heart Valves—Transluminal Catheter Implantation of a New Expandable Artificial Heart Valve in the Descending Thoracic Aorta in Isolated Vessels and Closed Chest Pigs, The International Journal of Artificial Organs, vol. 16, No. 5, pp. 253–262 (1993), submitted as Plaintiff Trial Exhibit 156 in C.A. No. 08–091–GMS in the District Court of Delaware.

Grube et al., First Report on a Human Percutaneous Transluminal Implantation of a Self–Expanding Valve Prosthesis for Interventional Treatment of Aortic Valve Stenosis, Catheterization and Cardiovascular Interventions, vol. 66, pp. 465–469 (2005) submitted as Plaintiff Trial Exhibit 158 in C.A. No. 08–091–GMS in the District Court of Delaware.

English Translation of French Patent 00 14028 submitted as Plaintiff Trial Exhibit 165 in C.A. No. 08–091–GMS in the District Court of Delaware.

Transcript of CoreValve analyst update conference call submitted as Plaintiff Trial Exhibit 168 in C.A. No. 08–091–GMS in the District Court of Delaware.

Photo of Edwards Sapien THV submitted as Plaintiff Trial Exhibit 258 in C.A. No. 08–091–GMS in the District Court of Delaware.

EC Design Examination Certificate Medical Device Directive submitted as Plaintiff Trial Exhibit 380 in C.A. No. 08–091–GMS in the District Court of Delaware.

First Witness Statement of Robrecht Michiels submitted as Plaintiff Trial Exhibit 401 in C.A. No. 08–091–GMS in the District Court of Delaware.

Andersen et al., Transluminal Hasenkam Hasenkam Implantation of artificial heart valves. Description of a new expandable aortic valve and initial results with implantation by catheter technique in closed chest pigs, European Heart Journal, vol. 13, pp. 704–708 (1992) submitted as Plaintiff Trial Exhibit 447 in C.A. No. 08–091–GMS in the District Court of Delaware.

Letter from Henning Rud Andersen to D. L. Brutsaert enclosing manuscript submission for European Heart Journal submitted as Plaintiff Trial Exhibit 523 in C.A. No. 08–091–GMS in the District Court of Delaware.

Andersen et al., Transluminal catheter implantation of a new expandable artificial cardiac valve in the aorta and the beating heart of closed chest pigs, European Heart Journal, vol. 11, p. 224 (Aug. 1990) submitted as Plaintiff Trial Exhibit 531 in C.A. No. 08–091–GMS in the District Court of Delaware.

Andersen et al., Implantation of Artificial Heart Valves (Manuscript), submitted as Plaintiff Trial Exhibit 532 in C.A. No. 08–091–GMS in the District Court of Delaware.

Letter from Simon Dack of JACC to Henning Andersen enclosing referee comments of manuscript (No. JAC000331) submitted as Plaintiff Trial Exhibit 533 in C.A. No. 08–091–GMS in the District Court of Delaware.

Letter from Simon Dack of JACC to Henning Andersen enclosing referee comments of manuscript (No. JAC000333) submitted as Plaintiff Trial Exhibit 534 in C.A. No. 08–091–GMS in the District Court of Delaware.

Letter from Ruth R. Ohman of JACC to Henning Andersen acknowledging receipt of manuscript (No. JAC000331) submitted as Plaintiff Trial Exhibit 535 in C.A. No. 08–091–GMS in the District Court of Delaware.

Rejection of article titled "Implantation of Artificial Heart Valves" submitted as Plaintiff Trial Exhibit 536 in C.A. No. 08–091–GMS in the District Court of Delaware.

Letter from Knud Tange Rasmussen of DTI to Kenneth H. Levin of C.R. Bard submitted as Plaintiff Trial Exhibit 537 in C.A. No. 08–091–GMS in the District Court of Delaware.

Letter from H. Anderson to S. Rowe re: developments of U.S. Patent No. 5,411,552 submitted as Plaintiff Trial Exhibit 544 in C.A. No. 08–091–GMS in the District Court of Delaware.

Fax from H. Anderson to S. Rowe attaching letter re: meeting to discuss possibilities for Johnson & Johnson to negotiate license agreement of U.S. Patent No. 5,411,552 submitted as Plaintiff Trial Exhibit 545 in C.A. No. 08–091–GMS in the District Court of Delaware.

Letter from H. Anderson to S. Rowe re: reimbursement of travel expenses submitted as Plaintiff Trial Exhibit 548 in C.A. No. 08–091–GMS in the District Court of Delaware.

Letter from H. Anderson to W. Sterman re Sep. 12, 1995 announcement regarding corporation between Heartport and St. Jude submitted as Plaintiff Trial Exhibit 565 in C.A. No. 08–091–GMS in the District Court of Delaware.

Letter from M. Garrison to H. Anderson re: renewed Heartport effort in endovascular valve replacement submitted as Plaintiff Trial Exhibit 566 in C.A. No. 08–091–GMS in the District Court of Delaware.

Letter from H. Anderson to M. Garrison re: development of invention by Heartport submitted as Plaintiff Trial Exhibit 567 in C.A. No. 08–091–GMS in the District Court of Delaware.

Edwards Endovascular HVT—Patriot submitted as Plaintiff Trial Exhibit 589 in C.A. No. 08–091–GMS in the District Court of Delaware.

L.L. Knudsen, H.R. Andersen & J.M. Hasenkam, Transluminal Catheter Implantation of a New Expandable Artificial Heart Valve in the Descending Thoracic Aorta in Isolated Vessels and Closed Chest Pigs (Abstract), submitted as Plaintiff Trial Exhibit 647 in C.A. No. 08–091–GMS in the District Court of Delaware.

H.R. Andersen et al., Abstract Submission Form for XII Congress of the European Society of Cardiology, Transluminal catheter implantation of a new expandable artificial cardiac valve (the stent–valve) in the aorta and the beating heart of closed chest pigs submitted as Plaintiff Trial Exhibit 683 in C.A. No. 08–091–GMS in the District Court of Delaware.

Excerpt from Abstracts from the 65th Scientific Sessions New Orleans Convention Center Nov. 16–19, 1992, Supplement to Circulation vol. 86, No. 4, 1–698 (Oct. 1992) submitted as Plaintiff Trial Exhibit 695 in C.A. No. 08–091–GMS in the District Court of Delaware.

Steven R. Bailey, Percutaneous Expandable Prosthetic Valves, Textbook of Interventional Cardiology, 2nd Edition, vol. 2, pp. 1268–1276 (1994) submitted as Plaintiff Trial Exhibit 700 in C.A. No. 08–091–GMS in the District Court of Delaware.

H. R. Andersen, Transluminal Catheter Implanted Prosthetic Heart Valves, Int'l of Angiology 7: 102–106 (1998) submitted as Plaintiff Trial Exhibit 708 in C.A. No. 08–091–GMS in the District Court of Delaware.

"Stent–Klappen" (Danish) Gris Nr. 1 submitted as Plaintiff Trial Exhibit 753 in C.A. No. 08–091–GMS in the District Court of Delaware with Stent–Valve Pig No. 1 (English Translation) submitted as Plaintiff Trial Exhibit 754 in C.A. No. 08–091–GMS in the District Court of Delaware.

"Stent–Klappen" (Danish) Gris Nr. 2 submitted as Plaintiff Trial Exhibit 755 in C.A. No. 08–091–GMS in the District Court of Delaware with Stent–Valve Pig No. 2 (English Translation) submitted as Plaintiff Trial Exhibit 756 in C.A. No. 08–091–GMS in the District Court of Delaware.

"Stent–Klappen" (Danish) Gris Nr. 3 submitted as Plaintiff Trial Exhibit 757 in C.A. No. 08–091–GMS in the District Court of Delaware with Stent–Valve Pig No. 3 (English Translation) submitted as Plaintiff Trial Exhibit 7586 in C.A. No. 08–091–GMS in the District Court of Delaware.

"Stent–Klappen" (Danish) Gris Nr. 4 submitted as Plaintiff Trial Exhibit 759 with Stent–Valve Pig No. 4 (English Translation) submitted as Plaintiff Trial Exhibit 760, "Stent–Klappen" (Danish) GRIS NR. 4 (with handwriting) submitted as Plaintiff Trial Exhibit 761 and Stent–Valve Pig No. 4 (English Translation) with handwriting submitted as Plaintiff Trial Exhibit 762 in C.A. No. 08–091–GMS in the District Court of Delaware.

"Stent–Klappen" (Danish) Gris Nr. 5 submitted as Plaintiff Trial Exhibit 763 with Stent–Valve Pig No. 5 (English Translation) submitted as Plaintiff Trial Exhibit 764, "Stent–Klappen" (Danish) GRIS NR. 5 (with handwriting) submitted as Plaintiff Trial Exhibit 765 and Stent–Valve Pig No. 5 (English Translation) with handwriting submitted as Plaintiff Trial Exhibit 766 in C.A. No. 08–091–GMS in the District Court of Delaware.

"Stent–Klappen" (Danish) Gris Nr. 6 submitted as Plaintiff Trial Exhibit 767 with Stent–Valve Pig No. 6 (English Translation) submitted as Plaintiff Trial Exhibit 768, "Stent–Klappen" (Danish) GRIS NR. 6 (with handwriting) submitted as Plaintiff Trial Exhibit 769 and Stent–Valve Pig No. 6 (English Translation) with handwriting submitted as Plaintiff Trial Exhibit 770 in C.A. No. 08–091–GMS in the District Court of Delaware.

"Stent–Klappen" (Danish) Gris Nr. 7 submitted as Plaintiff Trial Exhibit 771 in C.A. No. 08–091–GMS in the District Court of Delaware with Stent–Valve Pig No. 7 (English Translation) submitted as Plaintiff Trial Exhibit 772 in C.A. No. 08–091–GMS in the District Court of Delaware.

"Stent–Klappen" (Danish) Gris Nr. 8 submitted as Plaintiff Trial Exhibit 773 in C.A. No. 08–091–GMS in the District Court of Delaware with Stent–Valve Pig No. 8 (English Translation) submitted as Plaintiff Trial Exhibit 774 in C.A. No. 08–091–GMS in the District Court of Delaware.

"Stent–Klappen" (Danish) Gris Nr. 9 submitted as Plaintiff Trial Exhibit 775 in C.A. No. 08–091–GMS in the District Court of Delaware with Stent–Valve Pig No. 9 (English Translation) submitted as Plaintiff Trial Exhibit 776 in C.A. No. 08–091–GMS in the District Court of Delaware.

"Stent–Klappen" (Danish) Gris Nr. 10 submitted as Plaintiff Trial Exhibit 777 in C.A. No. 08–091–GMS in the District Court of Delaware with Stent–Valve Pig No. 10 (English Translation) submitted as Plaintiff Trial Exhibit 778 in C.A. No. 08–091–GMS in the District Court of Delaware.

"Stent–Klappen" (Danish) Gris Nr. 11 submitted as Plaintiff Trial Exhibit 779 in C.A. No. 08–091–GMS in the District Court of Delaware with Stent–Valve Pig No. 11 (English Translation) submitted as Plaintiff Trial Exhibit 780 in C.A. No. 08–091–GMS in the District Court of Delaware.

"Stent–Klappen" (Danish) Gris Nr. 12 submitted as Plaintiff Trial Exhibit 781 in C.A. No. 08–091–GMS in the District Court of Delaware with Stent–Valve Pig No. 12 (English Translation) submitted as Plaintiff Trial Exhibit 754 in C.A. No. 08–091–GMS in the District Court of Delaware.

"Stent–Klappen" (Danish) Gris Nr. 13 submitted as Plaintiff Trial Exhibit 783 in C.A. No. 08–091–GMS in the District Court of Delaware with Stent–Valve Pig No. 13 (English Translation) submitted as Plaintiff Trial Exhibit 784 in C.A. No. 08–091–GMS in the District Court of Delaware.

"Stent–Klappen" (Danish) Gris Nr. 14 submitted as Plaintiff Trial Exhibit 785 in C.A. No. 08–091–GMS in the District Court of Delaware with Stent–Valve Pig No. 14 (English Translation) submitted as Plaintiff Trial Exhibit 786 in C.A. No. 08–091–GMS in the District Court of Delaware.

"Stent–Klappen" (Danish) Gris Nr. 15 submitted as Plaintiff Trial Exhibit 787 in C.A. No. 08–091–GMS in the District Court of Delaware with Stent–Valve Pig No. 15 (English Translation) submitted as Plaintiff Trial Exhibit 788 in C.A. No. 08–091–GMS in the District Court of Delaware.

"Stent–Klappen" (Danish) Gris Nr. 16 submitted as Plaintiff Trial Exhibit 789 in C.A. No. 08–091–GMS in the District Court of Delaware with Stent–Valve Pig No. 16 (English Translation) submitted as Plaintiff Trial Exhibit 790 in C.A. No. 08–091–GMS in the District Court of Delaware.

"Stent–Klappen" (Danish) Gris Nr. 17 submitted as Plaintiff Trial Exhibit 791 in C.A. No. 08–091–GMS in the District Court of Delaware with Stent–Valve Pig No. 17 (English Translation) submitted as Plaintiff Trial Exhibit 792 in C.A. No. 08–091–GMS in the District Court of Delaware.

"Stent–Klappen" (Danish) Gris Nr. 18 submitted as Plaintiff Trial Exhibit 793 in C.A. No. 08–091–GMS in the District Court of Delaware with Stent–Valve Pig No. 18 (English Translation) submitted as Plaintiff Trial Exhibit 794 in C.A. No. 08–091–GMS in the District Court of Delaware.

"Stent–Klappen" (Danish) Gris Nr. 19 submitted as Plaintiff Trial Exhibit 795 in C.A. No. 08–091–GMS in the District Court of Delaware with Stent–Valve Pig No. 19 (English Translation) submitted as Plaintiff Trial Exhibit 796 in C.A. No. 08–091–GMS in the District Court of Delaware.

"Stent–Klappen" (Danish) Gris Nr. 20 submitted as Plaintiff Trial Exhibit 797 in C.A. No. 08–091–GMS in the District Court of Delaware with Stent–Valve Pig No. 20 (English Translation) submitted as Plaintiff Trial Exhibit 798 in C.A. No. 08–091–GMS in the District Court of Delaware.

"Stent–Klappen" (Danish) Gris Nr. 21 submitted as Plaintiff Trial Exhibit 799 in C.A. No. 08–091–GMS in the District Court of Delaware with Stent–Valve Pig No. 21 (English Translation) submitted as Plaintiff Trial Exhibit 800 in C.A. No. 08–091–GMS in the District Court of Delaware.

"Stent–Klappen" (Danish) Gris Nr. 22 submitted as Plaintiff Trial Exhibit 801 in C.A. No. 08–091–GMS in the District Court of Delaware with Stent–Valve Pig No. 22 (English Translation) submitted as Plaintiff Trial Exhibit 802 in C.A. No. 08–091–GMS in the District Court of Delaware.

"Stent–Klappen" (Danish) Gris Nr. 23 submitted as Plaintiff Trial Exhibit 803 in C.A. No. 08–091–GMS in the District Court of Delaware with Stent–Valve Pig No. 23 (English Translation) submitted as Plaintiff Trial Exhibit 804 in C.A. No. 08–091–GMS in the District Court of Delaware.

"Stent–Klappen" (Danish) Gris Nr. 24 submitted as Plaintiff Trial Exhibit 805 in C.A. No. 08–091–GMS in the District Court of Delaware with Stent–Valve Pig No. 24 (English Translation) submitted as Plaintiff Trial Exhibit 806 in C.A. No. 08–091–GMS in the District Court of Delaware.

"Stent–Klappen" (Danish) Gris Nr. 25 submitted as Plaintiff Trial Exhibit 807 in C.A. No. 08–091–GMS in the District Court of Delaware with Stent–Valve Pig No. 25 (English Translation) submitted as Plaintiff Trial Exhibit 808 in C.A. No. 08–091–GMS in the District Court of Delaware.

"Stent–Klappen" (Danish) undated Gris Nr. 26 submitted as Plaintiff Trial Exhibit 809 in C.A. No. 08–091–GMS in the District Court of Delaware with Stent–Valve Pig No. 26 (English Translation) undated submitted as Plaintiff Trial Exhibit 810 in C.A. No. 08–091–GMS in the District Court of Delaware and "Stent–Klappen" (Danish) Gris Nr. 26 submitted as Plaintiff Trial Exhibit 811 in C.A. No. 08–091–GMS in the District Court of Delaware with Stent–Valve Pig No. 26 (English Translation) submitted as Plaintiff Trial Exhibit 812 in C.A. No. 08–091–GMS in the District Court of Delaware.

"Stent–Klappen" (Danish) Gris Nr. 27 submitted as Plaintiff Trial Exhibit 813 in C.A. No. 08–091–GMS in the District Court of Delaware with Stent–Valve Pig No. 27 (English Translation) submitted as Plaintiff Trial Exhibit 814 in C.A. No. 08–091–GMS in the District Court of Delaware.

"Stent–Klappen" (Danish) Gris Nr. 28 submitted as Plaintiff Trial Exhibit 815 with Stent–Valve Pig No. 28 (English Translation) submitted as Plaintiff Trial Exhibit 816, "Stent–Klappen" (Danish) GRIS NR. 28 (with handwriting) submitted as Plaintiff Trial Exhibit 817 and Stent–Valve Pig No. 28 (English Translation) with handwriting submitted as Plaintiff Trial Exhibit 818 in C.A. No. 08–091–GMS in the District Court of Delaware.

"Stent–Klappen" (Danish) Gris Nr. 29 submitted as Plaintiff Trial Exhibit 819 in C.A. No. 08–091–GMS in the District Court of Delaware with Stent–Valve Pig No. 29 (English Translation) submitted as Plaintiff Trial Exhibit 820 in C.A. No. 08–091–GMS in the District Court of Delaware.

"Stent–Klappen" (Danish) Gris Nr. 30 submitted as Plaintiff Trial Exhibit 821 in C.A. No. 08–091–GMS in the District Court of Delaware with Stent–Valve Pig No. 30 (English Translation) submitted as Plaintiff Trial Exhibit 822 in C.A. No. 08–091–GMS in the District Court of Delaware.

"Stent–Klappen" (Danish) Gris Nr. 30B submitted as Plaintiff Trial Exhibit 823 in C.A. No. 08–091–GMS in the District Court of Delaware with Stent–Valve Pig No. 30B (English Translation) submitted as Plaintiff Trial Exhibit 824 in C.A. No. 08–091–GMS in the District Court of Delaware.

"Stent–Klappen" (Danish) Gris Nr. 31 submitted as Plaintiff Trial Exhibit 825 in C.A. No. 08–091–GMS in the District Court of Delaware with Stent–Valve Pig No. 31 (English Translation) submitted as Plaintiff Trial Exhibit 826 in C.A. No. 08–091–GMS in the District Court of Delaware.

"Stent–Klappen" (Danish) Gris Nr. 32 submitted as Plaintiff Trial Exhibit 827 in C.A. No. 08–091–GMS in the District Court of Delaware with Stent–Valve Pig No. 32 (English Translation) submitted as Plaintiff Trial Exhibit 828 in C.A. No. 08–091–GMS in the District Court of Delaware.

"Stent–Klappen" (Danish) Gris Nr. 33 submitted as Plaintiff Trial Exhibit 829 in C.A. No. 08–091–GMS in the District Court of Delaware with Stent–Valve Pig No. 33 (English Translation) submitted as Plaintiff Trial Exhibit 830 in C.A. No. 08–091–GMS in the District Court of Delaware.

"Stent–Klappen" (Danish) Gris Nr. 34 submitted as Plaintiff Trial Exhibit 831 in C.A. No. 08–091–GMS in the District Court of Delaware with Stent–Valve Pig No. 34 (English Translation) submitted as Plaintiff Trial Exhibit 832 in C.A. No. 08–091–GMS in the District Court of Delaware.

"Stent–Klappen" (Danish) Gris Nr. 35 submitted as Plaintiff Trial Exhibit 833 in C.A. No. 08–091–GMS in the District Court of Delaware with Stent–Valve Pig No. 35 (English Translation) submitted as Plaintiff Trial Exhibit 834 in C.A. No. 08–091–GMS in the District Court of Delaware.

"Stent–Klappen" (Danish) Gris Nr. 36 submitted as Plaintiff Trial Exhibit 835 in C.A. No. 08–091–GMS in the District Court of Delaware with Stent–Valve Pig No. 36 (English Translation) submitted as Plaintiff Trial Exhibit 836 in C.A. No. 08–091–GMS in the District Court of Delaware.

"Stent–Klappen" (Danish) Gris Nr. 37 submitted as Plaintiff Trial Exhibit 837 in C.A. No. 08–091–GMS in the District Court of Delaware with Stent–Valve Pig No. 37 (English Translation) submitted as Plaintiff Trial Exhibit 838 in C.A. No. 08–091–GMS in the District Court of Delaware.

"Stent–Klappen" (Danish) Gris Nr. 38 submitted as Plaintiff Trial Exhibit 839 in C.A. No. 08–091–GMS in the District Court of Delaware with Stent–Valve Pig No. 38 (English Translation) submitted as Plaintiff Trial Exhibit 840 in C.A. No. 08–091–GMS in the District Court of Delaware.

"Stent–Klappen" (Danish) Gris Nr. 39 submitted as Plaintiff Trial Exhibit 841 in C.A. No. 08–091–GMS in the District Court of Delaware with Stent–Valve Pig No. 39 (English Translation) submitted as Plaintiff Trial Exhibit 842 in C.A. No. 08–091–GMS in the District Court of Delaware.

"Stent–Klappen" (Danish) Gris Nr. 40 submitted as Plaintiff Trial Exhibit 843 in C.A. No. 08–091–GMS in the District Court of Delaware with Stent–Valve Pig No. 40 (English Translation) submitted as Plaintiff Trial Exhibit 844 in C.A. No. 08–091–GMS in the District Court of Delaware.

"Stent–Klappen" (Danish) Gris Nr. 41 submitted as Plaintiff Trial Exhibit 845 in C.A. No. 08–091–GMS in the District Court of Delaware with Stent–Valve Pig No. 41 (English Translation) submitted as Plaintiff Trial Exhibit 846 in C.A. No. 08–091–GMS in the District Court of Delaware.

Collection of letters between P. Block, M. Chan, and H.R. Andersen submitted as Plaintiff Trial Exhibit 851 in C.A. No. 08–091–GMS in the District Court of Delaware.

"Stent–Klappen" (Danish) submitted as Plaintiff Trial Exhibit 852 in C.A. No. 08–091–GMS in the District Court of Delaware with English translation to be agreed upon by the parties submitted as Plaintiff Trial Exhibit 852A in C.A. No. 08–091–GMS in the District Court of Delaware.

"Stent–Klappen" (Danish) submitted as Plaintiff Trial Exhibit 853 in C.A. No. 08–091–GMS in the District Court of Delaware with English translation to be agreed upon by the parties submitted as Plaintiff Trial Exhibit 853A in C.A. No. 08–091–GMS in the District Court of Delaware.

"En Ny Kateterbaren Stent–Monterer Kunstig Hjerteklap Til Implantation Uden Aben Hjertekirurgi" (Danish) submitted as Plaintiff Trial Exhibit 860 in C.A. No. 08–091–GMS in the District Court of Delaware with English translation to be agreed upon by the parties submitted as Plaintiff Trial Exhibit 860A in C.A. No. 08–091–GMS in the District Court of Delaware.

Andersen et al., Implantation of Artificial Heart Valves (manuscript) submitted as Plaintiff Trial Exhibit 861 in C.A. No. 08–091–GMS in the District Court of Delaware.

Letter from Henning Rud Andersen to Knud Tange Rasmussen of DTI (Danish) submitted as Plaintiff Trial Exhibit 863 in C.A. No. 08–091–GMS in the District Court of Delaware with English translation to be agreed upon by the parties submitted as Plaintiff Trial Exhibit 863A in C.A. No. 08–091–GMS in the District Court of Delaware.

Letter from Hans Rasmussen of DTI to Henning Rud Andersen (Danish) submitted as Plaintiff Trial Exhibit 865 in C.A. No. 08–091–GMS in the District Court of Delaware with English Translation to be agreed upon by the parties submitted as Plaintiff Trial Exhibit 865A in C.A. No. 08–091–GMS in the District Court of Delaware.

Letter from Henning Rud Andersen to Knud Tange Rasmussen of DTI (Danish) submitted as Plaintiff Trial Exhibit 866 in C.A. No. 08–091–GMS in the District Court of Delaware with English translation submitted as Plaintiff Trial Exhibit 866A in C.A. No. 08–091–GMS in the District Court of Delaware.

Letter from Henning Rud Andersen to Knud Tange Rasmussen of DTI (Danish) submitted as Plaintiff Trial Exhibit 867 in C.A. No. 08–091–GMS in the District Court of Delaware with English translation submitted as Plaintiff Trial Exhibit 867A in C.A. No. 08–091–GMS in the District Court of Delaware.

Letter from Henning Rud Andersen to Knud Tange Rasmussen of DTI (Danish) submitted as Plaintiff Trial Exhibit 868 in C.A. No. 08–091–GMS in the District Court of Delaware with English Translation submitted as Plaintiff Trial Exhibit 868A in C.A. No. 08–091–GMS in the District Court of Delaware.

Miscellaneus data sheets from Pig No. 17 (Danish) submitted as Plaintiff Trial Exhibit 869 in C.A. No. 08–091–GMS in the District Court of Delaware.

"Dansk Cardiologisk Selskab's" (Danish) submitted as Plaintiff Trial Exhibit 870 in C.A. No. 08–091–GMS in the District Court of Delaware with English Translation submitted as Plaintiff Trial Exhibit 870A in C.A. No. 08–091–GMS in the District Court of Delaware.

Letter from Henning Rud Andersen to Per Holm of Vingmed A/S (Danish) submitted as Plaintiff Trial Exhibit 871 in C.A. No. 08–091–GMS in the District Court of Delaware with English Translation submitted as Plaintiff Trial Exhibit 871A in C.A. No. 08–091–GMS in the District Court of Delaware.

Letter from Henning Rud Andersen to Peter De Jong of Baxter submitted as Plaintiff Trial Exhibit 872 in C.A. No. 08–091–GMS in the District Court of Delaware.

Letter from Henning Rud Andersen to Niels Christiansen of Pfizer (Danish) submitted as Plaintiff Trial Exhibit 873 in C.A. No. 08–091–GMS in the District Court of Delaware with English Translation submitted as Plaintiff Trial Exhibit 837A in C.A. No. 08–091–GMS in the District Court of Delaware.

Letter from Hans Rasmussen of DTI to Henning Rud Andersen (Danish) submitted as Plaintiff Trial Exhibit 874 in C.A. No. 08–091–GMS in the District Court of Delaware with English Translation submitted as Plaintiff Trial Exhibit 874A in C.A. No. 08–091–GMS in the District Court of Delaware.

Letter from Henning Rud Andersen to Kaj Berlich of Baxter (Danish) submitted as Plaintiff Trial Exhibit 875 in C.A. No. 08–091–GMS in the District Court of Delaware with English Translation submitted as Plaintiff Trial Exhibit 875A in C.A. No. 08–091–GMS in the District Court of Delaware.

Letter from Per Holm on Vingmed A/S to Henning Rud Andersen (Danish) submitted as Plaintiff Trial Exhibit 876 in C.A. No. 08–091–GMS in the District Court of Delaware with English Translation submitted as Plaintiff Trial Exhibit 876A in C.A. No. 08–091–GMS in the District Court of Delaware.

Letter from Henning Rud Andersen to Niels Christiansen of Pfizer (Danish) submitted as Plaintiff Trial Exhibit 877 in C.A. No. 08–091–GMS in the District Court of Delaware with English translation submitted as Plaintiff Trial Exhibit 877A in C.A. No. 08–091–GMS in the District Court of Delaware.

Letter from Per Holm of Vingmed A/S to Peter Chevalier of Medtronic, Inc. (Danish) submitted as Plaintiff Trial Exhibit 878 in C.A. No. 08–091–GMS in the District Court of Delaware with English Translation submitted as Plaintiff Trial Exhibit 878A in C.A. No. 08–091–GMS in the District Court of Delaware.

Fax from Peter Chevalier of Medtronic, Inc. to Per Holm of Vingmed A/S submitted as Plaintiff Trial Exhibit 879 in C.A. No. 08–091–GMS in the District Court of Delaware.

Letter from Bent Holmegaand of Meadox Surgimed A/S to Knud Tange Rasmussen of DTI (Danish) submitted as Plaintiff Trial Exhibit 881 in C.A. No. 08–091–GMS in the District Court of Delaware with English Translation submitted as Plaintiff Trial Exhibit 881A in C.A. No. 08–091–GMS in the District Court of Delaware.

Letter from Knud Tange Rasmussen of DTI to Henning Rud Andersen (Danish) submitted as Plaintiff Trial Exhibit 882 in C.A. No. 08–091–GMS in the District Court of Delaware with English Translation submitted as Plaintiff Trial Exhibit 882A in C.A. No. 08–091–GMS in the District Court of Delaware.

Letter from Kenneth H. Levin of C.R. Bard, Inc. to Hemming [sic] Reid [sic] Andersen submitted as Plaintiff Trial Exhibit 883 in C.A. No. 08–091–GMS in the District Court of Delaware.

Letter from Henning Rud Andersen to Knud Tange rasmussen of DTI (Danish) submitted as Plaintiff Trial Exhibit 884 in C.A. No. 08–091–GMS in the District Court of Delaware with English translation submitted as Plaintiff Trial Exhibit 884A in C.A. No. 08–091–GMS in the District Court of Delaware.

Letter from Henning Rud Andersen to Kenneth Levin of C.R. Bard, Inc. submitted as Plaintiff Trial Exhibit 885 in C.A. No. 08–091–GMS in the District Court of Delaware.

Letter from Flemming Hoj Sorensen of DTI to Henning Rud Andersen (Danish) submitted as Plaintiff Trial Exhibit 886 in C.A. No. 08–091–GMS in the District Court of Delaware with English Translation submitted as Plaintiff Trial Exhibit 886A in C.A. No. 08–091–GMS in the District Court of Delaware.

Fax from Kenneth H. Levin of C.R. Bard, Inc. to Henning Rud Andersen submitted as Plaintiff Trial Exhibit 887 in C.A. No. 08–091–GMS in the District Court of Delaware.

Letter from Flemming Hoj Sorensen of DTI (Danish) submitted as Plaintiff Trial Exhibit 888 in C.A. No. 08–091–GMS in the District Court of Delaware with English Translation submitted as Plaintiff Trial Exhibit 888A in C.A. No. 08–091–GMS in the District Court of Delaware.

Letter from Flemming Hoj Sorensen and Knud Tange Rasmussen of DTI (Danish) submitted as Plaintiff Trial Exhibit 890 in C.A. No. 08–091–GMS in the District Court of Delaware with English Translation submitted as Plaintiff Trial Exhibit 890A in C.A. No. 08–091–GMS in the District Court of Delaware.

Letter from Henning Rud Andersen to MArcel van den Brand of Erasmus University Hospital submitted as Plaintiff Trial Exhibit 891 in C.A. No. 08–091–GMS in the District Court of Delaware.

Letter from Knud Tange Rasmussen of DTI to Henning Rud Andersen (Danish) submitted as Plaintiff Trial Exhibit 892 in C.A. No. 08–091–GMS in the District Court of Delaware with English Translation submitted as Plaintiff Trial Exhibit 892A in C.A. No. 08–091–GMS in the District Court of Delaware.

Letter from Knud Tange Rasmussen of DTI to Henning Rud Andersen (Danish) submitted as Plaintiff Trial Exhibit 893 in C.A. No. 08–091–GMS in the District Court of Delaware with English Translation submitted as Plaintiff Trial Exhibit 893A in C.A. No. 08–091–GMS in the District Court of Delaware.

Letter from Lars Lyhne Knudsen to Professor P. Sleigh enclosing manuscripts for review by Cardiovascular Research submitted as Plaintiff Trial Exhibit 894 in C.A. No. 08–091–GMS in the District Court of Delaware.

Letter from Knud Tange Rasmussen of DTI to Kenneth H. Levin of C.R. Bard submitted as Plaintiff Trial Exhibit 895 in C.A. No. 08–091–GMS in the District Court of Delaware.

Letter from Knud Tange Rasmussen of DTI to Henning Rud Andersen (Danish) submitted as Plaintiff Trial Exhibit 896 in C.A. No. 08–091–GMS in the District Court of Delaware with English Translation submitted as Plaintiff Trial Exhibit 896A in C.A. No. 08–091–GMS in the District Court of Delaware.

Letter from Marvin P. Loeb of Trimedyne to Henning Rud Andersen submitted as Plaintiff Trial Exhibit 897 in C.A. No. 08–091–GMS in the District Court of Delaware.

Letter from Knud Tange Rasmussen of DTI to Erik Andersen of Boston Scientific (Danish) submitted as Plaintiff Trial Exhibit 898 in C.A. No. 08–091–GMS in the District Court of Delaware with English Translation submitted as Plaintiff Trial Exhibit 898A in C.A. No. 08–091–GMS in the District Court of Delaware.

Letter from Henning Rud Andersen to Marvin P. Loeb of Trimedyne, Inc. submitted as Plaintiff Trial Exhibit 899 in C.A. No. 08–091–GMS in the District Court of Delaware.

Letter from Henning Rud Andersen to SCIMED submitted as Plaintiff Trial Exhibit 900 in C.A. No. 08–091–GMS in the District Court of Delaware.

Letter from Henning Rud Anderson to to Marvin P. Loeb of Trimedyne, Inc. submitted as Plaintiff Trial Exhibit 901 in C.A. No. 08–091–GMS in the District Court of Delaware.

Letter from Erik Andersen of Boston Scientific to Dansk Teknologisk Institut (Danish) submitted as Plaintiff Trial Exhibit 902 in C.A. No. 08–091–GMS in the District Court of Delaware with English Translation submitted as Plaintiff Trial Exhibit 902A in C.A. No. 08–091–GMS in the District Court of Delaware.

Letter from Marvin P. Loeb of Trimedyne, Inc. to Hanning Rud Andersen submitted as Plaintiff Trial Exhibit 903 in C.A. No. 08–091–GMS in the District Court of Delaware.

Letter from Henning Rud Andersen to Knud Tange Rasmussen of DTI submitted as Plaintiff Trial Exhibit 904 in C.A. No. 08–091–GMS in the District Court of Delaware.

Letter from Knud Tange Rasmussen of DTI to Henning Rud Andersen (Danish) submitted as Plaintiff Trial Exhibit 905 in C.A. No. 08–091–GMS in the District Court of Delaware.

Letter from Tamar J. Preminger of Children's Hospital (Boston) to Henning R. Andersen submitted as Plaintiff Trial Exhibit 906 in C.A. No. 08–091–GMS in the District Court of Delaware.

Letter from Henning Ruder Andersen to Tamar J. Preminger of Children's Hospital submitted as Plaintiff Trial Exhibit 907 in C.A. No. 08–091–GMS in the District Court of Delaware.

Letter from Marvin P. Loeb ot Trimedyne, Inc. to Rasmus Offersen of DTI submitted as Plaintiff Trial Exhibit 908 in C.A. No. 08–091–GMS in the District Court of Delaware.

Letter from Rasmus Offersen of DTI to Kurt Anker Jensen of Astra Meditek A/S (Danish) submitted as Plaintiff Trial Exhibit 909 in C.A. No. 08–091–GMS in the District Court of Delaware with English Translation submitted as Plaintiff Trial Exhibit 909A in C.A. No. 08–091–GMS in the District Court of Delaware.

Letter from Rasmus Offersen of DTI to Henning Rud Andersen (Danish) submitted as Plaintiff Trial Exhibit 910 in C.A. No. 08–091–GMS in the District Court of Delaware with English Translation submitted as Plaintiff Trial Exhibit 910A in C.A. No. 08–091–GMS in the District Court of Delaware.

Letter from Rasmus Offersen of DTI to Marvin P. Loeb of Trimedyne, Inc. submitted as Plaintiff Trial Exhibit 911 in C.A. No. 08–091–GMS in the District Court of Delaware.

Letter from Rasmus Offersen of DTI to Kurt Anker Jensen of Astra Meditek A/S (Danish) submitted as Plaintiff Trial Exhibit 912 in C.A. No. 08–091–GMS in the District Court of Delaware with English translation submitted as Plaintiff Trial Exhibit 912A in C.A. No. 08–091–GMS in the District Court of Delaware.

Letter from Rasmus Offersen of DTI to Peter Selley of Astra Tech AB (Danish) submitted as Plaintiff Trial Exhibit 915 in C.A. No. 08–091–GMS in the District Court of Delaware with English Translation submitted as Plaintiff Trial Exhibit 915A in C.A. No. 08–091–GMS in the District Court of Delaware.

Fax from Rasmus Offersen of DTI to Peter Selley of Astra Tech AB (Danish) submitted as Plaintiff Trial Exhibit 916 in C.A. No. 08–091–GMS in the District Court of Delaware with English Translation submitted as Plaintiff Trial Exhibit 916A in C.A. No. 08–091–GMS in the District Court of Delaware.

Letter from American Heart Association to Henning Rud Andersen concerning poster presentation acceptance submitted as Plaintiff Trial Exhibit 917 in C.A. No. 08–091–GMS in the District Court of Delaware.

Letter from Henning Rud Andersen to Rasmus Offersen of DTI (Danish) submitted as Plaintiff Trial Exhibit 918 in C.A. No. 08–091–GMS in the District Court of Delaware with English Ttranslation submitted as Plaintiff Trial Exhibit 918A in C.A. No. 08–091–GMS in the District Court of Delaware.

Fax from Rasmus Offersen of DTI to Wes Sterman of Stanford Surgical Technologies submitted as Plaintiff Trial Exhibit 919 in C.A. No. 08–091–GMS in the District Court of Delaware.

Letter from Rasmus Offersen of DTI to Wesley Sterman of Stanford Surgical Technologies, Inc. submitted as Plaintiff Trial Exhibit 920 in C.A. No. 08–091–GMS in the District Court of Delaware.

Letter from Lars Lynhne Knudsen to Eli A. Friedman of ASAIO Journal of enclosing manuscript for review submitted as Plaintiff Trial Exhibit 922 in C.A. No. 08–091–GMS in the District Court of Delaware.

Letter from Rasmus Offersen of DTI to Marvin P. Loeb of Trimedyne, Inc.submitted as Plaintiff Trial Exhibit 923 in C.A. No. 08–091–GMS in the District Court of Delaware.

Letter from Diego Brancaccio of Int'l Journal of Artificial Organs to Lars L. Knudsen concerning publication of manuscript submitted as Plaintiff Trial Exhibit 924 in C.A. No. 08–091–GMS in the District Court of Delaware.

Fax from Rasmus Offersen of DTI to Wesley Sterman of Stanford Surgical Technologies enclosing executed licensing agreement submitted as Plaintiff Trial Exhibit 925 in C.A. No. 08–091–GMS in the District Court of Delaware.

Letter from Henning Rud Andersen to Wesley Sterman of Stanford Surgical Technologies, Inc. submitted as Plaintiff Trial Exhibit 926 in C.A. No. 08–091–GMS in the District Court of Delaware.

Letter from Henning Rud Andersen to Hanson Giffort of Stanford Surgical Technologies, Inc. submitted as Plaintiff Trial Exhibit 927 in C.A. No. 08–091–GMS in the District Court of Delaware.

Letter from Tamar J. Preminger of Children's Hospital (Boston) to Henning Rud Andersen submitted as Plaintiff Trial Exhibit 929 in C.A. No. 08–091–GMS in the District Court of Delaware.

Letter from Ted Feldman of the University of Chicago to H. Rud Andersen submitted as Plaintiff Trial Exhibit 930 in C.A. No. 08–091–GMS in the District Court of Delaware.

Letter from Henning Rud Andersen to Tamar J. Preminger of Children's Hospital (Boston) submitted as Plaintiff Trial Exhibit 931 in C.A. No. 08–091–GMS in the District Court of Delaware.

Letter from Robert F. Kuhling of Onset Ventures to Leif Nielsen of Lehman & Ree submitted as Plaintiff Trial Exhibit 932 in C.A. No. 08–091–GMS in the District Court of Delaware.

Letter from Robert F. Kuhling of Onset Ventures to Henning Rud Andersen submitted as Plaintiff Trial Exhibit 933 in C.A. No. 08–091–GMS in the District Court of Delaware.

Letter from Henning Rud Andersen to Robert F. Kuhling of Onset Ventures submitted as Plaintiff Trial Exhibit 934 in C.A. No. 08–091–GMS in the District Court of Delaware.

Letter from Henning Rud Andersen to Wesley D. Sterman of Heartport, Inc. submitted as Plaintiff Trial Exhibit 935 in C.A. No. 08–091–GMS in the District Court of Delaware.

Letter from from Peter C. Block of St. Vincent's Medical Center to Henning Rud Andersen submitted as Plaintiff Trial Exhibit 936 in C.A. No. 08–091–GMS in the District Court of Delaware.

Letter from Peter C. Block of St. Vincents's Medical Center to Henning Rud Andersen submitted as Plaintiff Trial Exhibit 937 in C.A. No. 08–091–GMS in the District Court of Delaware.

Letter from Henning Rud Andersen to Peter C. Block of St. Vincent's Medical Center submitted as Plaintiff Trial Exhibit 938 in C.A. No. 08–091–GMS in the District Court of Delaware.

Letter from Peter C. Block of St. Vincents's Medical Center to Henning Rud Andersen submitted as Plaintiff Trial Exhibit 939 in C.A. No. 08–091–GMS in the District Court of Delaware.

Letter from Henning Rud Andersen to Peter C. Block of St. Vincent's Medical Center submitted as Plaintiff Trial Exhibit 940 in C.A. No. 08–091–GMS in the District Court of Delaware.

Letter from Henning Rud Andersen to Rasmus Offersen of DTI (Danish) submitted as Plaintiff Trial Exhibit 941 in C.A. No. 08–091–GMS in the District Court of Delaware with English Translation submitted as Plaintiff Trial Exhibit 941A in C.A. No. 08–091–GMS in the District Court of Delaware.

Letter from Peter C. Block of St. Vincent's Medical Center to Henning Rud Andersen submitted as Plaintiff Trial Exhibit 942 in C.A. No. 08–091–GMS in the District Court of Delaware.

Letter from Dusan Pavenik to Henning Rud Andersen submitted as Plaintiff Trial Exhibit 943 in C.A. No. 08–091–GMS in the District Court of Delaware.

Letter from Henning Rud Andersen to George Teitelbaum submitted as Plaintiff Trial Exhibit 944 in C.A. No. 08–091–GMS in the District Court of Delaware.

Letter from Henning Rud Andersen to Jan Peregrin submitted as Plaintiff Trial Exhibit 945 in C.A. No. 08–091–GMS in the District Court of Delaware.

Letter from Jeffry J. Grainger of Hearport, Inc. to Vibeke Walde of DTI submitted as Plaintiff Trial Exhibit 949 in C.A. No. 08–091–GMS in the District Court of Delaware.

Letter from Henning Rud Andersen to Jeffry Grainger of Heartport, Inc. submitted as Plaintiff Trial Exhibit 951 in C.A. No. 08–091–GMS in the District Court of Delaware.

Letter from Jan Komtebedde to Andersen et al. re: update on license agreement submitted as Plaintiff Trial Exhibit 953 in C.A. No. 08–091–GMS in the District Court of Delaware.

Consent to Merger Agreement between Heartport, Inc. and Andersen et al. submitted as Plaintiff Trial Exhibit 954 in C.A. No. 08–091–GMS in the District Court of Delaware.

Email chain from Vibeke Walde to Henning Rud Andersen re: VS: Andersen license (Danish in part) submitted as Plaintiff Trial Exhibit 956 in C.A. No. 08–091–GMS in the District Court of Delaware.

PVT Design Review—$1^{st}$ Design Iteration submitted as Plaintiff Trial Exhibit 1005 in C.A. No. 08–091–GMS in the District Court of Delaware.

Emails from Hanne Rask Hansen to Abi Zakai re: Collaboration submitted as Plaintiff Trial Exhibit 1013 in C.A. No. 08–091–GMS in the District Court of Delaware.

In vivo picture of CoreValve device, excerpted from CoreValve Slide Presentation of two heart valve prostheses in patients at Albert Einstein Hospital in Sao Paulo, Brazil submitted as Plaintiff Trial Exhibit 1078 in C.A. No. 08–091–GMS in the District Court of Delaware.

French Catheter Scales submitted as Plaintiff Trial Exhibit 1083 in C.A. No. 08–091–GMS in the District Court of Delaware.

PVT, Inc. Series B Convertible Preferred Stock Purchase Agreement b/w PVT and Medtronic submitted as Plaintiff Trial Exhibit 1092 in C.A. No. 08–091–GMS in the District Court of Delaware.

*Edwards Lifesciences AG* v. *Cook Biotech, Inc.* (HC 08C00934)—UK trial transcripts—Day 1–5 submitted as Plaintiff Trial Exhibit 1178 in C.A. No. 08–091–GMS in the District Court of Delaware.

Heartport Consent to Merger with Johnson & Johnson and HP Merger Sub submitted as Plaintiff Trial Exhibit 1556 in C.A. No. 08–091–GMS in the District Court of Delaware.

Disclosure Statement between Edwards and PVT (Dec. 15, 2003) submitted as Plaintiff Trial Exhibit 1563 in C.A. No. 08–091–GMS in the District Court of Delaware.

Certificate of Merger between PVT and Edwards submitted as Plaintiff Trial Exhibit 1565 in C.A. No. 08–091–GMS in the District Court of Delaware.

PVT Amended and Restated Certificate of Incorporation (Oct. 8, 2004) submitted as Plaintiff Trial Exhibit 1567 in C.A. No. 08–091–GMS in the District Court of Delaware.

Certification of Stanton Rowe (Jun. 15, 2007) submitted as Plaintiff Trial Exhibit 1572 in C.A. No. 08–091–GMS in the District Court of Delaware.

California Statement by Domestic Stock Corporation (Stanford Surgical) submitted as Plaintiff Trial Exhibit 1573 in C.A. No. 08–091–GMS in the District Court of Delaware.

Certificate of Filing Merger between Stanford Surgical and Hearport submitted as Plaintiff Trial Exhibit 1574 in C.A. No. 08–091–GMS in the District Court of Delaware.

Consent to Assignment between Stanford Surgical and Inventors submitted as Plaintiff Trial Exhibit 1575 in C.A. No. 08–091–GMS in the District Court of Delaware.

Edwards Sapien Transcatheter Heart Valve with RetroFlex 3 Transfermoral Kit submitted as Plaintiff Trial Exhibit 1630 in C.A. No. 08–091–GMS in the District Court of Delaware.

Presentation Business Review–Maunfacturing submitted as Plaintiff Trial Exhibit 1635 in C.A. No. 08–091–GMS in the District Court of Delaware.

Printout of List of Centers and Country (Excel) submitted as Plaintiff Trial Exhibit 1654A in C.A. No. 08–091–GMS in the District Court of Delaware.

Report—Leading the way to the next frontier of the cardio vascular device industry submitted as Plaintiff Trial Exhibit 1712 in C.A. No. 08–091–GMS in the District Court of Delaware.

Report—Leading the way to the next frontier of the cardio vascular device industry: Percutaneous aortic heart valve replacement submitted as Plaintiff Trial Exhibit 1713 in C.A. No. 08–091–GMS in the District Court of Delaware.

Colin Stewart, How Rob Michiels and Corevalve got where they are today, The Orange County register, submitted as Plaintiff Trial Exhibit 1747 in C.A. No. 08–091–GMS in the District Court of Delaware.

Financial Frontier for the years ending Dec. 21, 2007–2012 submitted as Plaintiff Trial Exhibit 1748 in C.A. No. 08–091–GMS in the District Court of Delaware.

"Edwards Lifesciences: Speed Bumps Ahead for Sapien, Downgrading to Underweight," North America Equity Research submitted as Plaintiff Trial Exhibit 1807 in C.A. No. 08–091–GMS in the District Court of Delaware.

Print–out—Corevalve reporting—Apr. 2005—Version 1 (Excel) submitted as Plaintiff Trial Exhibit 1900A in C.A. No. 08–091–GMS in the District Court of Delaware.

PVT Press Release—Heartport Announces Exclusive Licensing Agreement with Percutaneous Valve Technologies submitted as Plaintiff Trial Exhibit 1968 in C.A. No. 08–091–GMS in the District Court of Delaware.

Medical Device Daily, vol. 10, No. 60 submitted as Plaintiff Trial Exhibit 20303 in C.A. No. 08–091–GMS in the District Court of Delaware.

Corevalve press release: CoreValve Completes $24 Million Series B Round of Financing Led by Apax Partners submitted as Plaintiff Trial Exhibit 2031 in C.A. No. 08–091–GMS in the District Court of Delaware.

Corevalve press release: CoreValve Completes $33 Million Private Financing submitted as Plaintiff Trial Exhibit 2032 in C.A. No. 08–091–GMS in the District Court of Delaware.

In Strategy Shift, CoreValve to Manufacture Device in U.S. Facility, Dow Jone VentureWire submitted as Plaintiff Trial Exhibit 2033 in C.A. No. 08–091–GMS in the District Court of Delaware.

CoreValve, Inc. Financial Forecas submitted as Plaintiff Trial Exhibit 2034 in C.A. No. 08–091–GMS in the District Court of Delaware.

Edward's CE Marking of Conformity Certificate submitted as Plaintiff Trial Exhibit 2059 in C.A. No. 08–091–GMS in the District Court of Delaware.

Edwards' EC–Design Examination Certificate submitted as Plaintiff Trial Exhibit 2060 in C.A. No. 08–091–GMS in the District Court of Delaware.

Patient Selection for the CoreValve ReValving System by Ganesh Mahoharan et al. submitted as Plaintiff Trial Exhibit 2090 in C.A. No. 08–091–GMS in the District Court of Delaware.

Presentation—France Registry: French Aortic National CoreValve and Edwards Registry, Helene Eltchaninoff submitted as Plaintiff Trial Exhibit 2123 in C.A. No. 08–091–GMS in the District Court of Delaware.

CE Markings of Conformity issued to Edwards Lifesciences submitted as Plaintiff Trial Exhibit 2124 in C.A. No. 08–091–GMS in the District Court of Delaware.

Color Photographs of Andersen et al. stent valve and related materials submitted as Plaintiff Trial Exhibit 2129 in C.A. No. 08–091–GMS in the District Court of Delaware.

Color Photographs of Andersen et al. stent valve and related materials submitted as Plaintiff Trial Exhibit 2130 in C.A. No. 08–091–GMS in the District Court of Delaware.

Color Photographs of Andersen et al. stent valve and related materials submitted as Plaintiff Trial Exhibit 2131 in C.A. No. 08–091–GMS in the District Court of Delaware.

Color Photographs of Andersen et al. stent valve and related materials submitted as Plaintiff Trial Exhibit 2132 in C.A. No. 08–091–GMS in the District Court of Delaware.

Handwritten notes made by Dr. Buller on CoreValve device during his direct testimony (top view) submitted as Plaintiff Trial Exhibit 2135 in C.A. No. 08–091–GMS in the District Court of Delaware.

Handwritten notes made by Dr. Buller on CoreValve device during his direct testimony (side view) submitted as Plaintiff Trial Exhibit 2136 in C.A. No. 08–091–GMS in the District Court of Delaware.

Handwritten notes made by Dr. Buller on CoreValve device during his direct testimony (side view) submitted as Plaintiff Trial Exhibit 2137 in C.A. No. 08–091–GMS in the District Court of Delaware.

CoreValve's Timeline: Actual vs. No Infringement submitted as Plaintiff Trial Exhibit 2141 in C.A. No. 08–091–GMS in the District Court of Delaware.

CoreValve's Timeline: Actual vs. No Infringement (Europe) submitted as Plaintiff Trial Exhibit 2142 in C.A. No. 08–091–GMS in the District Court of Delaware.

Edwards' Damages—*Lost Profits Units* vs. *Reasonable Royalty Units* (Europe) submitted as Plaintiff Trial Exhibit 2143 in C.A. No. 08–091–GMS in the District Court of Delaware.

Summary of Edwards' Damages in Europe submitted as Plaintiff Trial Exhibit 2144 in C.A. No. 08–091–GMS in the District Court of Delaware.

Summary of Edwards' Lost Profits submitted as Plaintiff Trial Exhibit 2145 in C.A. No. 08–091–GMS in the District Court of Delaware.

Summary of Edwards' Total Damages submitted as Plaintiff Trial Exhibit 2146 in C.A. No. 08–091–GMS in the District Court of Delaware.

Reasonable Royalty if No Lost Profits submitted as Plaintiff Trial Exhibit 2147 in C.A. No. 08–091–GMS in the District Court of Delaware.

Translation of Letter from K. Rasmussen to H. Andersen re Novelty Search on Implantable Stent Valve, dated Oct. 25, 1989, submitted as Plaintiff Trial Exhibit 7 in C.A. No. 08–091–GMS in the District Court of Delaware.

Article: "Transluminal Implantation of Artificial Heart Valves Description of a New Expandable Aortic Valve and Initial 1992 Results with Implantation by Catheter Technique in Closed Chest Pigs", European Heart Journal, vol. 13, pp. 704–708, pp. 704–708, by H. Andersen, L. Knudsen and J. Hasenkam, dated 1992 submitted as Defendant Trial Exhibit 14 in C.A. No. 08–091–GMS in the District Court of Delaware.

Letter from D.L. Brutsaert to H. Andersen re Manuscript Entitled "Transluminal Implantation of Artificial Heart Valves" Accepted for Publication, dated Oct. 3, 1991 submitted as Defendant Trial Exhibit 17 in C.A. No. 08–091–GMS in the District Court of Delaware.

Letter from J. Fabricius to Danish Institute of Technology re Opinion on "Stent Valve Project" dated Mar. 5, 1990 Letter from H. Andersen to K. Rasmussen re Comments on Written Opinion from Fabricius, dated May 15, 1990 submitted as Defendant Trial Exhibit 42 in C.A. No. 08–091–GMS in the District Court of Delaware.

Letter from S. Dack to H. Andersen re Hasenkam Hasenkam Rejection of Manuscript Entitled "Implantation of Artificial Heart Valves" dated Jul. 26, 1990 submitted as Defendant Trial Exhibit 48 in C.A. No. 08–091–GMS in the District Court of Delaware.

Drawing by Witness of Stent Prototype submitted as Defendant Trial Exhibit 57 in C.A. No. 08–091–GMS in the District Court of Delaware.

Report: "Development, Manufacture, and in Vitro and In Vivo Evaluation of an Artificial Heart Valve for Implantation Using the Catheter Technique with a View to Future Intravasal Treatment of Heart Valve Disorders", by L. Knudsen, dated 1992 submitted as Defendant Trial Exhibit 60 in C.A. No. 08–091–GMS in the District Court of Delaware.

Article: "Catheter—Implanted Prosthetic Heart Valves—Transluminal Catheter Implantation of a New Expandable Artificial Heart Valve in the Descending Thoracic Aorta in Isolated Vessels and Closed Chest Pigs", The International Journal of Artificial Organs, vol. 16, pp. 253–262, by L. Knudsen, H. Andersen, & J. Hasenkam, dated 1993 submitted as Defendant Trial Exhibit 61 in C.A. No. 08–091–GMS in the District Court of Delaware.

Powerpoint Presentation: "Percutaneous Rowe–Rowe–Valve Technologies" by A. Cribier, M. Leon, S. Rabinovich & S. Rowe submitted as Defendant Trial Exhibit 76 in C.A. No. 08–091–GMS in the District Court of Delaware.

Document: "Percutaneous Valve Technologies, Inc. Business Plan," dated Feb. 2000 submitted as Defendant Trial Exhibit 81 in C.A. No. 08–091–GMS in the District Court of Delaware.

Drawing of CAD Design for the Production of Two Stents, dated Jan. 2, 2000 submitted as Defendant Trial Exhibit 84 in C.A. No. 08–091–GMS in the District Court of Delaware.

Report: "Design Review—Concept Phase," dated May 15, 200 submitted as Defendant Trial Exhibit 85 in C.A. No. 08–091–GMS in the District Court of Delaware.

Report: "R & D Monthly Report—Jun. 2000," dated Jun. 13, 2000 submitted as Defendant Trial Exhibit 87 in C.A. No. 08–091–GMS in the District Court of Delaware.

Letter from H. Gifford to H. Andersen re Endovascular Valve Replacement Porcedure, dated Sep. 29, 1993 submitted as Defendant Trial Exhibit 97 in C.A. No. 08–091–GMS in the District Court of Delaware.

PowerPoint Slides of PHV Frame Evolution submitted as Defendant Trial Exhibit 102 in C.A. No. 08–091–GMS in the District Court of Delaware.

Exhibit "SR–7" referred to in the First Witness Statement of Station Rowe dated May 27, 2008 submitted as Defendant Trial Exhibit 103 in C.A. No. 08–091–GMS in the District Court of Delaware.

Document: "PVT Stent Follow–Up Table" submitted as Defendant Trial Exhibit 104 in C.A. No. 08–091–GMS in the District Court of Delaware.

Document: "Outlines of a Research Program for the Development of an Implantable Heart Valve (1HV)" submitted as Defendant Trial Exhibit 207 in C.A. No. 08–091–GMS in the District Court of Delaware.

Document: "Non–Surgical Cardiac Valve Implantation" submitted as Defendant Trial Exhibit 211 in C.A. No. 08–091–GMS in the District Court of Delaware.

Document: Conception Review–Prosthesis Design Conception, dated May 5, 2004 submitted as Defendant Trial Exhibit 239 in C.A. No. 08–091–GMS in the District Court of Delaware.

U.S. Patent No. 7,018,406 B2, entitled "Prosthetic Valve for Transluminal Delivery" issued to Sequin et al on Mar. 28, 2006 with attached file history, submitted as Defendant Trial Exhibit 289 in C.A. No. 08–091–GMS in the District Court of Delaware.

Pig experiments of Drs. Andersen, Hasenkam, and Knudsen submitted as Defendant Trial Exhibit 294 in C.A. No. 08–091–GMS in the District Court of Delaware.

Color version of Test Report and signature page of #R–2006–006: Frame Deflection and Leaflet Angle–Core Valve Percutaneous Aortic Valve Generation 3, 26 mm (Previously produced black and white image COR674610–674633) submitted as Defendant Trial Exhibit 1313 in C.A. No. 08–091–GMS in the District Court of Delaware.

Color version of Report and signature page for Protocol #R–2006–010: Frame Deflection and Leaflet Angle–Core Valve Percutaneous Aortic Valve Generation 3, 29 mm (Previously produced black and white image COR680225–680238) submitted as Defendant Trial Exhibit 1314 in C.A. No. 08–091–GMS in the District Court of Delaware.

Contact Sheet of photographs of CoreValve prototypes taken by Edwards' counsel on Janu 25, 2010 submitted as Defendant Trial Exhibit 1459 in C.A. No. 08–091–GMS in the District Court of Delaware.

Picture of Physical Device submitted as Defendant Trial Exhibit 1460 in C.A. No. 08–091–GMS in the District Court of Delaware.

Picture of Physical Device submitted as Defendant Trial Exhibit 1462 in C.A. No. 08–091–GMS in the District Court of Delaware.

Picture of Physical Device submitted as Defendant Trial Exhibit 1466 in C.A. No. 08–091–GMS in the District Court of Delaware.

Picture of Physical Device submitted as Defendant Trial Exhibit 1467 in C.A. No. 08–091–GMS in the District Court of Delaware.

Picture of Generation 1 CoreValve device submitted as Defendant Trial Exhibit 1469 in C.A. No. 08–091–GMS in the District Court of Delaware.

Picture of Physical Device submitted as Defendant Trial Exhibit 1471 in C.A. No. 08–091–GMS in the District Court of Delaware.

Picture of Physical Device submitted as Defendant Trial Exhibit 1473 in C.A. No. 08–091–GMS in the District Court of Delaware.

Timeline re CoreValve would have made all its Sales overseas—Fall 2004 start date submitted as Defendant Trial Exhibit 1478 in C.A. No. 08–091–GMS in the District Court of Delaware.

Timeline re CoreValve would have made all its Sales overseas—Spring 2005 start date submitted as Defendant Trial Exhibit 1479 in C.A. No. 08-091-GMS in the District Court of Delaware.
Jeffery Kinrich demonstrative graphic submitted as Defendant Trial Exhibit 1483 in C.A. No. 08-091-GMS in the District Court of Delaware.
Jeffery Kinrich demonstrative graphic submitted as Defendant Trial Exhibit 1484 in C.A. No. 08-091-GMS in the District Court of Delaware.
Jeffery Kinrich demonstrative graphic submitted as Defendant Trial Exhibit 1485 in C.A. No. 08-091-GMS in the District Court of Delaware.
Jeffery Kinrich demonstrative graphic submitted as Defendant Trial Exhibit 1486 in C.A. No. 08-091-GMS in the District Court of Delaware.
Jeffery Kinrich demonstrative graphic submitted as Defendant Trial Exhibit 1487 in C.A. No. 08-091-GMS in the District Court of Delaware.
Order Construing the Terms of U.S. Patent Nos. 5,411,552, 6,168,614 and 6,582,462 in *Edwards Lifesciences AG and Edwards Lifesciences, LLC v. Medtronic CoreValve LLC,* United States District Court for the District of Delaware, Civil Action No. 1:08-CV-00091-GMS, May 27, 2009.
Order in *Edwards Lifesciences AG and Edwards Lifesciences, LLC v. Medtronic CoreValve LLC,* United States District Court for the District of Delaware, Civil Action No. 1:08-CV-00091-GMS, Mar. 22, 2010.
Office Communication, Aug. 7, 2009, U.S. Appl. No. 90/009,484.
Office Action, Mar. 10, 2009, U.S. Appl. No. 10/268,253.
Affidavit of Michael Gadeberg, Jul. 8, 2010.
Amendment Accompanying An RCE, Oct. 31, 2007, U.S. Appl. No. 10/268,253.
Office Action, May 5, 2009, U.S. Appl. No. 10/268,253.
Office Action, Feb. 27, 2007, U.S. Appl. No. 10/268,253.
Office Action, Dec. 3, 2003, U.S. Appl. No. 10/268,253.
Office Action, Jul. 9, 2010, U.S. Appl. No. 12/557,458.
Slide Deck for Plaintiff's Opening Statement in *Edwards Lifesciences AG and Edwards Lifesciences, LLC v. Medtronic CoreValve LLC,* United States District Court for the District of Delaware, Civil Action No. 1:08-CV-00091-GMS, Mar. 23, 2010.
Plaintiff's Trial Exhibit 2135, *Edwards Lifesciences AG and Edwards Lifesciences, LLC v. Medtronic CoreValve LLC,* United States District Court for the District of Delaware, Civil Action No. 1:08-CV-00091-GMS, Mar. 26, 2010.
Slide Deck for Plaintiff's Closing Arguments in *Edwards Lifesciences AG and Edwards Lifesciences, LLC v. Medtronic CoreValve LLC,* United States District Court for the District of Delaware, Civil Action No. 1:08-CV-00091-GMS, Apr. 1, 2010.
Revised Slides for Plaintiff's Closing Arguments in *Edwards Lifesciences AG and Edwards Lifesciences, LLC v. Medtronic CoreValve LLC,* United States District Court for the District of Delaware, Civil Action No. 1:08-CV-00091-GMS, Apr. 1, 2010.
U.S. Appl. No. 95/001,615, filed May 4, 2011, Andersen et al.
U.S. Appl. No. 95/001,616, filed May 4, 2011, Andersen et al.
U.S. Appl. No. 90/009,791, filed Jul. 29, 2010, Andersen et al.
U.S. Appl. No. 90/009,779, filed Jul. 9, 2010, Andersen et al.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claim 1 is confirmed.

Claims 2-8 were not reexamined.

* * * * *